US007774252B2

(12) United States Patent
Seare et al.

(10) Patent No.: US 7,774,252 B2
(45) Date of Patent: Aug. 10, 2010

(54) METHOD AND SYSTEM FOR GENERATING STATISTICALLY-BASED MEDICAL PROVIDER UTILIZATION PROFILES

(75) Inventors: Jerry G. Seare, Sandy, UT (US); Patricia A. Smith-Wilson, Herriman, UT (US); Kurt Van Wagoner, Centerville, UT (US); Jean A. Mattey, Westlake, OH (US); Eileen K. Synder, Sandy, UT (US); Candace C. Wahlstrom, Twin Falls, ID (US); Michelle Willis, Sandy, UT (US); Matthew R. Bentley, South Jordan, UT (US)

(73) Assignee: Ingenix, Inc., Eden Prairie, MN (US)

( * ) Notice: Subject to any disclaimer, the term of this patent is extended or adjusted under 35 U.S.C. 154(b) by 452 days.

(21) Appl. No.: 11/512,003

(22) Filed: Aug. 29, 2006

(65) Prior Publication Data
US 2006/0293922 A1 Dec. 28, 2006

Related U.S. Application Data

(60) Continuation of application No. 09/437,567, filed on Nov. 10, 1999, now Pat. No. 7,222,079, which is a continuation of application No. 08/539,413, filed on Oct. 5, 1995, now Pat. No. 6,223,164, which is a division of application No. 08/264,795, filed on Jun. 23, 1994, now Pat. No. 5,557,514.

(51) Int. Cl.
*G06Q 40/00* (2006.01)
(52) U.S. Cl. .................... 705/35; 705/3; 705/4
(58) Field of Classification Search ............ 705/10–44, 705/1–5, 30–35
See application file for complete search history.

(56) References Cited

U.S. PATENT DOCUMENTS

| 4,328,491 | A | 5/1982 | Demetrescu et al. |
| 4,491,725 | A | 1/1985 | Pritchard |
| 4,667,292 | A | 5/1987 | Mohlenbrock et al. |
| 5,018,067 | A | 5/1991 | Mohlenbrock et al. |

(Continued)

FOREIGN PATENT DOCUMENTS

WO    WO 95/12857    5/1995

OTHER PUBLICATIONS

Mainour, Arch G., et al. "Antibiotics for Colds in Children who are the High Prescribers?", *American Journal of Diseases of Children*, Apr. 1998.
Cave, Douglas G., Ph.D. MPH, 1994, "Pattern-of-Treatment Differences Among Primary Care Physicians in Alternative Systems of Care", *Benefits Quarterly*, 10(3):6-19.
Horner, Ronnie D., "Accuracy of patient encounter and billing information in ambulatory care", *Journal of Family Practice*, vol. 33, No. 6, p. 593(6), Dec. 1991.

*Primary Examiner*—Frantzy Poinvil
(74) *Attorney, Agent, or Firm*—Dorsey & Whitney LLP; Adriana S. Luedke

(57) ABSTRACT

A method and system for analyzing historical medical provider billings to statistically establish a normative utilization profile. Comparison of a medical provider's utilization profile with a normative profile is enabled. Based on historical treatment patterns and a fee schedule, an accurate model of the cost of a specific medical episode can be created. Various treatment patterns for a particular diagnosis can be compared by treatment cost and patient outcome to determine the most cost-effective treatment approach. It is also possible to identify those medical providers who provide treatment that does not fall within the statistically established treatment patterns or profiles.

4 Claims, 12 Drawing Sheets

U.S. PATENT DOCUMENTS

| | | |
|---|---|---|
| 5,099,424 A | 3/1992 | Schneiderman |
| 5,225,976 A | 7/1993 | Tawil |
| 5,253,164 A | 10/1993 | Holloway et al. |
| 5,301,105 A | 4/1994 | Cummings, Jr. |
| 5,307,262 A | 4/1994 | Ertel |
| 5,324,077 A | 6/1994 | Kessler et al. |
| 5,325,293 A | 6/1994 | Dorne |
| 5,365,425 A | 11/1994 | Torma et al. |

METHOD AND SYSTEM FOR GENERATING STATISTICALLY-BASED MEDICAL PROVIDER UTILIZATION PROFILES

CROSS-REFERENCE TO RELATED APPLICATION(S)

This application is a continuation of U.S. application Ser. No. 09/437,567, filed on Nov. 10, 1999, now issued as U.S. Pat. No. 7,222,079, which is a continuation of U.S. application Ser. No. 08/539,413, filed on Oct. 5, 1995, now issued U.S. Pat. No. 6,223,164, which is a divisional of U.S. application Ser. No. 08/264,795, filed on Jun. 23, 1994, now issued as U.S. Pat. No. 5,557,514, the contents of which are incorporated in their entirety by reference herein.

MICROFICHE APPENDIX

This specification includes a Microfiche Appendix which includes 1 page of microfiche with a total of 37 frames. The microfiche appendix includes computer source code of one preferred embodiment of the invention. In other embodiments of the invention, the inventive concept may be implemented in other computer code, in computer hardware, in other circuitry, in a combination of these, or otherwise. The Microfiche Appendix is hereby incorporated by reference in its entirety and is considered to be a part of the disclosure of this specification.

I. BACKGROUND OF INVENTION

A. Field of the Invention

The invention relates to methods and systems for analyzing medical claims histories and billing patterns to statistically establish treatment utilization patterns for various medical services. Data is validated using statistical and clinically derived methods. Based on historical treatment patterns and a fee schedule, an accurate model of the cost of a specific medical episode can be created. Various treatment patterns for a particular diagnosis can be compared by treatment cost and patient outcome to determine the most effective treatment approach. It is also possible to identify those medical providers who provide treatment that does not fall within the statistically established treatment patterns or profiles.

B. The Background Art

It is desirable to compare claims for reimbursement for medical services against a treatment pattern developed from a large body of accurate medical provider billing history information. Although in the prior art some attempt was made to compare claims for reimbursement for medical services to a normative index, the prior art did not construct the normative index based on actual clinical data. Rather, the prior art based the normative index on a subjective conception (such as the medical consensus of a specialty group) of what the proper or typical course of treatment should be for a given diagnosis. Such prior art normative indices tended to vary from the reality of medical practice. In the prior art, automated medical claims processing systems, systems for detecting submission of a fraudulent medical claims, and systems for providing a medical baseline for the evaluation of ambulatory medical services were known. Documents which may be relevant to the background of the invention, including documents pertaining to medical reimbursement systems, mechanisms for detecting fraudulent medical claims, and related analytical and processing methods, were known. Examples include: U.S. Pat. No. 4,858,121, entitled "Medical Payment System" and issued in the name Barber et al. on Aug. 15, 1989; U.S. Pat. No. 5,253,164, entitled "System and Method for Detecting Fraudulent Medical Claims Via Examination of Service Codes" and issued in the name of Holloway et al. on Oct. 12, 1993; U.S. Pat. No. 4,803,641, entitled "Basic Expert System Tool" and issued in the name of Hardy et al. on Feb. 7, 1989; U.S. Pat. No. 5,658,370, entitled "Knowledge Engineering Tool" and issued in the name of Erman et al. on Apr. 14, 1987; U.S. Pat. No. 4,667,292, entitled "Medical Reimbursement Computer System" and issued in the name of Mohlenbrock et al. on May 19, 1987; U.S. Pat. No. 4,858,121, entitled "Medical Payment System" and issued in the name of Barber et al. on Aug. 15, 1989; and U.S. Pat. No. 4,987,538, entitled "Automated Processing of Provider Billings" and issued in the name of Johnson et al. on Jan. 22, 1991, each of which is hereby incorporated by reference in its entirety for the material disclosed therein.

Additional examples of documents that may be relevant to the background of the invention are: Leape, "Practice Guidelines and Standards: An Overview," *QRB* (February 1990); Jollis et al., "Discordance of Databases Designed for Claims Payment versus Clinical Information Systems," *Annals of Internal Medicine* (Oct. 15, 1993); Freed et al., "Tracking Quality Assurance Activity," *American College of Utilization Review Physicians* (November, 1988); Roberts et al., "Quality and Cost-Efficiency," *American College of Utilization Review Physicians* (November, 1988), Rodriguez, "Literature Review," *Quality Assurance and Utilization Review-Official Journal of the American College of Medical Quality* (Fall 1991); Elden, "The Direction of the Healthcare Marketplace," *Journal of the American College of Utilization Review Physicians* (August 1989); Rodriguez, "Literature Review," *Quality Assurance and Utilization Review-Official Journal of the American College of Medical Quality* (Fall 1991); Roos et al., "Using Administrative Data to Predict Important Health Outcomes," *Medical Care* (March 1988); Burns et al., "The Use of Continuous Quality Improvement Methods in the Development and Dissemination of Medical Practice Guidelines, *QRB* (December, 1992); Weingarten, "The Case for Intensive Dissemination: Adoption of Practice Guidelines in the Coronary Care Unit," *QRB* (December, 1992); Flagle et al., "AHCPR-NLM Joint Initiative for Health Services Research Information: 1992 Update on OHSRI," *QRB* (December, 1992); Holzer, "The Advent of Clinical Standards for Professional Liability," *QRB* (February, 1990); Gottleib et al., "Clinical Practice Guidelines at an HMO: Development and Implementation in a Quality Improvement Model," *QRB* (February, 1990); Borbas et al., "The Minnesota Clinical Comparison and Assessment Project," *QRB* (February, 1990); Weiner et al., "Applying Insurance Claims Data to Assess Quality of Care: A Compilation of Potential Indicators," *QRB* (December, 1990); Wakefield et al., "Overcoming the Barriers to Implementation of TQM/CQI in Hospitals: Myths and Realities," *QRB* (March, 1993); Donabedian, "The Role of Outcomes in Quality Assessment and Assurance," *QRB* (November, 1992); Dolan et al., "Using the Analytic Hierarchy Process (AHP) to Develop and Disseminate Guidelines," *QRB* (December, 1992); Hadorn et al., "An Annotated Algorithm Approach to Clinical Guideline Development," *JAMA* (Jun. 24, 1992); Falconer et al., "The Critical Path Method in Stroke Rehabilitation: Lessons from an Experiment in Cost Containment and Outcome Improvement," *QRB* (January, 1993); Reinertsen, "Outcomes Management and Continuous Quality Improvement: The Compass and the Rudder," *QRB* (January, 1993); Mennemeyer, "Downstream Outcomes: Using Insurance Claims Data to Screen for Errors in Clinical Laboratory Testing," *QRB* (June, 1991); Iezzoni, "Using Severity Information for Quality Assessment: A Review of Three Cases by Five Severity Measures," QRB (December 1989); Kahn, "Measuring the Clinical Appropriateness of the Use of a Procedure," *Medical Care* (April, 1988); Wall, "Practice Guidelines: Promise or Panacea?," *The Journal of Family Practice* (1993); Lawless, "A Managed Care Approach to Outpatient Review," *Quality Assurance and Utilization Review-Official Journal of the American College of Utilization Review Physicians* (May, 1990); Dragalin et al., "Institutes for Quality: Prudential's Approach to Outcomes Management for Specialty Procedures," QRB (March, 1990); Chinsky, "patterns of Treatment Ambulatory Health Care Management, Physician Profiling—The Impact of Physician, Patient, and Market Characteristics On Appropriateness of Physician Practice in the Ambulatory Setting," (Doctoral Dissertation, The University of Michigan, 1991), published by Concurrent Review Concurrent Review Technology, Inc., Shingle Springs, Calif.; "Patterns of Treatment Ambulatory Health Care Management, Implementation Guide," published by Concurrent Review Concurrent Review Technology, Inc., Shingle Springs, Calif.; "Patterns of Treatment Ambulatory Health Care Management, Patterns Processing Model," published by Concurrent Review Concurrent Review Technology, Inc., Shingle Springs, Calif.; *Report on Medical Guidelines & Outcome Research*, 4 (Feb. 11, 1993); "Practice Guidelines—The Experience of Medical Specialty Societies," *United States General Accounting Office Report to Congressional Reguestors*(*GAO/PEMD*-91-11 *Practice Guideline*) (Feb. 21, 1991); "Medicare Intermediary Manual Part 3—Claims Process," *Department of Health and Human Services, Health Care Financing Administration, Transmittal No.* 1595 (April 1993); *CCH Pulse The Health Care Reform Newsletter* (Apr. 19, 1993); Winslow, "Report Card on Quality and Efficiency of HMOs May Provide a Model for Others," *The Wall Street Journal*; Jencks et al., "Strategies for Reforming Medicare's Physician Payments," *The New England Journal of Medicine* (Jun. 6, 1985); Solon et al., "Delineating Episodes of Medical Care," *A.J.P.H.* (March, 1967); Health Care (September, 1986) (the entire issue of Volume 24, Number 9, Supplement); Miller et al., "Physician Charges in the Hospital," *Medical Care* (July, 1992); Garnick, "Services and Charges by PPO Physicians for PPO and Indemnity Patients," *Medical Care* (October, 1990); Hurwicz et al., "Care Seeking for Musculoskeletal and Respiratory Episodes in a Medicare Population," *Medical Care* (November, 1991); Gold, "The Content of Adult Primary Care Episodes," *Public Health Reports* (January-February, 1982); Welch et al., "Geographic Variations in Expenditures for Physicians' Services in the United States," *The New England Journal of Medicine* (Mar. 4, 1993); Schneeweiss et al., "Diagnosis Clusters: A New Tool for Analyzing the Content of Ambulatory Medical Care," *Medical Care* (January, 1983); Showstack, "Episode-of-Care Physician Payment: A Study of Cornorary Arter Bypass Graft Surgery," *Inquiry* (Winter, 1987); Schappert, "National Ambulatory Medical Survey: 1989 Summary," *Vital and Health Statistics. U.S. Department of Health and Human Services, Public Health Service, Centers for Disease Control, National Center for Health Statistics* (April, 1992) (DHHS Publication No. [PHS] 92-1771); Graves, "Detailed Diagnoses and Procedures, National Hospital Discharge Survey, 1990," *Vital and Health Statistics, U.S. Department of Health and Human Services. Public Health Service, Centers for Disease Control, National Center for Health Statistics* (June, 1992) (DHHS Publication No. [PHS] 92-1774); "National Hospital Discharge Survey: Annual Summary, 1990," *Vital and Health Statistics, U.S. Department of Health and Human Services, Public Health Service, Centers for Disease Control, National Center for Health Statistics* (June, 1992) (DHHS Publication No. [PHS] 92-1773); "Prevalence of Selected Chronic Conditions: United States, 1986-88," *Vital and Health Statistics, U.S. Department of Health and Human Services, Public Health Service, Centers for Disease Control, National Center for Health Statistics* (February, 1993) (Series 10, No. 182); "Current Estimates From the National Health Interview Survey, 1991," *Vital and Health Statistics, U.S. Department of Health and Human Services, Public Health Service, Centers for Disease Control, National Center for Health Statistics* (February, 1993) (DHHS Publication No. [PHS] 93-1512); Iezzoni et al., "A Description and Clinical Assessment of the Computerized Severity Index," *QRB* (February, 1992); *Health Care Financing Review*, p. 30 (Winter, 1991); *Statistical Abstract of the United States* (1992); and *Health and Prevention Profile—United States* (1991) (published by U.S. Department of Health and Human Services, Public Health Service, Centers for Disease Control, National Center for Health Studies), each of which is hereby incorporated by reference in its entirety for the material disclosed therein.

Additional background materials to which the reader is directed for both background and to refer to while studying this specification include: *Physicians' Current Procedural Terminology CPT* '94, published by American Medical Association, *Code it Right Techniques for Accurate Medical Coding*, published by Medicode Inc., *HCPCS* 1994 *Medicare's National Level II Codes*, published by Medicode Inc., *MedIndex ICD 9 CM Fourth Edition* 1993, published by MedIndex, each of which is hereby incorporated by reference in its entirety for the material disclosed therein.

II. SUMMARY OF THE INVENTION

It is an object to provide a mechanism for assessing medical services utilization patterns. The invention achieves this object by allowing comparison processing to compare an individual treatment or a treatment group against a statistical norm or against a trend.

It is an object of the invention to provide a mechanism for converting raw medical providers billing data into an informative historical database. The invention achieves this object by read, analyze and merge ("RAM") processing coupled with claims edit processing to achieve a reliable, relevant data set.

It is an object of the invention to provide a mechanism for accurately determining an episode of care. The invention achieves this object by providing a sequence of steps which, when performed, yield an episode of care while filtering out irrelevant and inapplicable data.

It is an object of the invention to provide a method for performing a look-up of information, that is, providing a mechanism for gaining access to different parts of the informational tables maintained in the database. This object is achieved by reviewing the referenced tables for specific codes representing specific diagnoses. The codes are verified for accuracy. Then tables are accessed to display selected profiles. Users are then given the opportunity to select profiles for comparison.

It is an object of the invention to provide a method for comparing profiles. This object is achieved by comparing index codes against historical reference information stored in the parameter tables. Discovered information is checked against defined statistical criteria in the parameter tables. The process is repeated for each index code and its profile developed in the history process as many times as necessary to complete the information gathering.

It is an object of the invention to create, maintain and present to the user a variety of report products. These reports are provided either on-line or in a hard copy format. The process of creating, maintaining and presenting these reports is designed to present relevant information in a complete and useful manner.

It is an object of the invention to provide a mechanism for creating a practice parameter database. This object is achieved in the invention by repetitive episode of care processing and entry of processed episode of care data into a data table until the populated data table becomes the practice parameter database.

III. BRIEF DESCRIPTION OF THE DRAWINGS

IV. DETAILED DESCRIPTION OF THE PREFERRED EMBODIMENT

Figure 1:
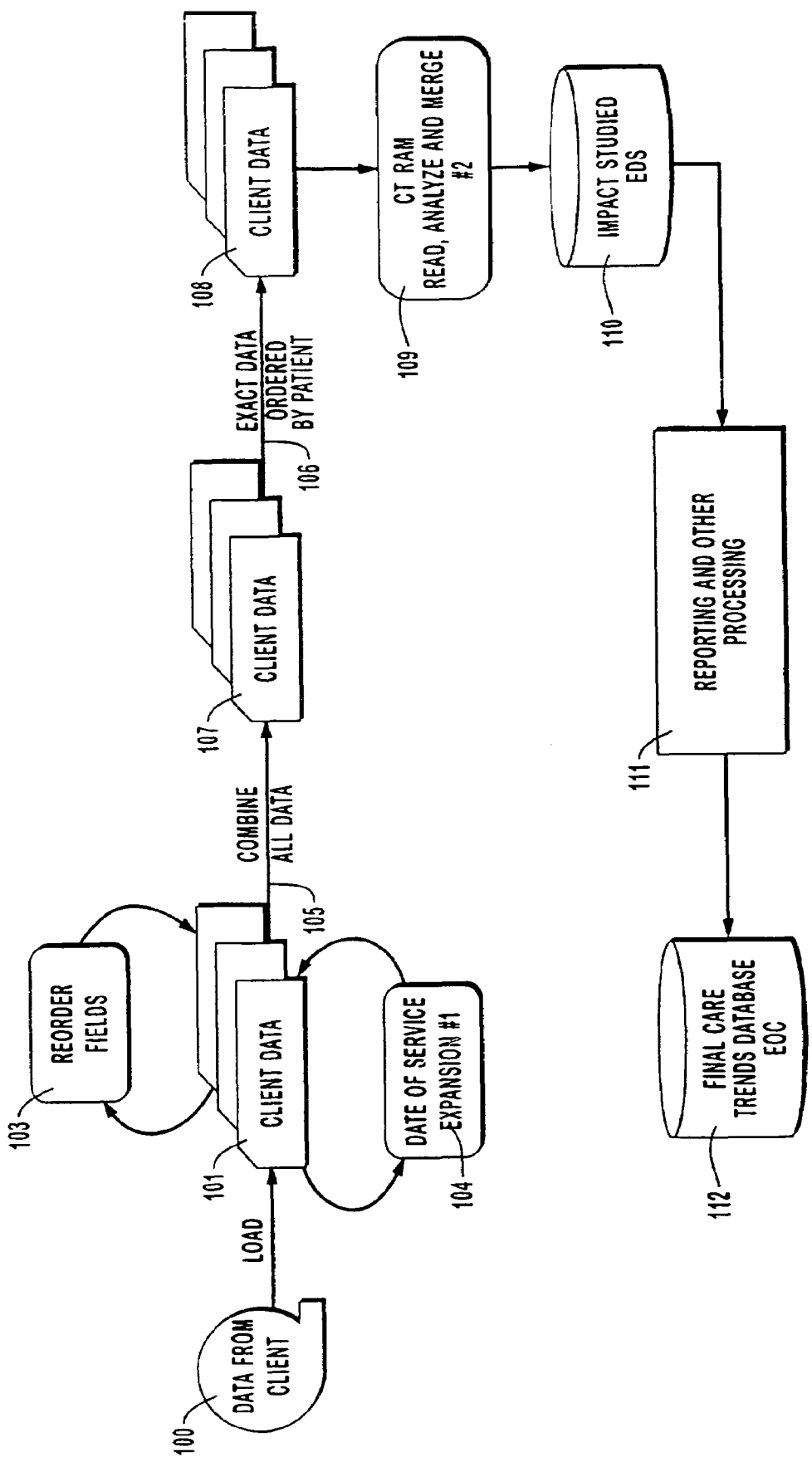
FIG. 1 depicts steps performed in the method of the invention to establish a practice parameter or utilization profile for a particular diagnosis.

The invention includes both a system and a method for analyzing healthcare providers' billing patterns, enabling an assessment of medical services utilization patterns. When the invention is employed, it can readily be seen whether a provider or multiple providers are overutilizing or underutilizing services when compared to a particular historical statistical profile. The statistical profile of the invention is a statically-derived norm based on clinically-validated data which has been edited to eliminate erroneous or misleading information. The profiles may be derived from geographic provider billing data, national provider billing data, the provider billing data of a particular payor entity (such as an insurance company) or various other real data groupings or sets. Twenty informational tables are used in the database of the preferred embodiment of the invention. These include a Procedure Description Table, ICD-9 Description Table, Index Table, Index Global Table, Index Detail Table, Window Table, Procedure Parameter Table, Category Table, Qualifying Master Table, Specialty Table, Zip/Region Table, Family Table, Specialty Statistic Table, Age/Gender Statistic Table, Region Statistic Table, Qualifying Index Table, Qualifying Group Table, Category Parameter Table, Duration Parameter Table and Family Table. ICD 9 codes or ICD (International Classification of Diseases, generically referred to as a disease classification) codes as they are generally referred to herein are used in the preferred embodiment. In other embodiments of the invention other codes could be used, such as: predecessors or successors to ICD codes or substitutes therefor, such as DSM 3 codes, SNOWMED codes, or any other diagnostic coding schemes. These tables are described in detail as follows. It should be noted, however, that these tables describe are used by the inventors in one implementation of the invention, and that the inventive concept described herein may be implemented in a variety of ways.

Procedure Description Table

This table identifies and validates five years of both CPT (Current Procedural Terminology, generically referred to as an identifying code for reporting a medical service) and HCPCS level II procedure codes. The lifetime occurrence maximum and follow-up days associated with a procedure code are also located in this table.

| | | | |
|---|---|---|---|
| Code(Key) | Alpha/Numeric | 5 | Standard CPT or HCPCS(5 Years including Modifiers) |
| Sub-Code | Character | 2 | * = Starred Procedures<br>N = New Codes Current Year<br>D1 = Deleted Code Current Year<br>D2 = Deleted Code Previous Year<br>D3 = Deleted Code Third Year<br>D4 = Deleted Code Fourth Year<br>C = Changed Description |
| Life Time Occurrence | Numeric | 2 | Number = Count of occurrence in a lifetime<br>Blank = Not applicable |
| Follow Up Days | Numeric | 3 | Number of Follow up Days to procedure. |
| Description | Character | 48 | Standard abbreviated description |
| Total | | 60 | |

Use:

This table can validate CPT and HCPCs codes.

Five years of codes will be kept.

Give a brief description of the code.

Gives the maximum number of occurrences that this code can be done in a lifetime, if applicable. (Programming not addressed, to date)

Give the number of follow up days to a procedure. (Programming not addressed, to date)

Modifiers are stored in this table with a "099" prefix (i.e., the 80 modifier is "09980") with a description of the modifier.

This table interrelates with:
  Parameter Tables
  Category Table
  Qualifying Tables
  Specialty Table
  CPT Statistic Table Source:

This table is taken from the TB_PROC table from gendbs from prod1. The occurrence field is maintained by the Medicode staff.

ICD-9 Description Table

This table identifies and validates five years of diagnosis codes. It also contains a risk adjustment factor for each diagnosis.

| | | | |
|---|---|---|---|
| ICD-9 Code(Key) | Alpha/Numeric | 5 | Left justified, assumed decimal after 3rd position |
| Sub-Code | Character | 2 | N = New Code<br>D = Deleted Code<br>C = Changed Code |
| Indicator | Character | 1 | * or blank<br>* = code requires 4th and/or 5th digits to be specific |
| Risk | Alpha/Numeric | 2 | Overall Classification of Disease |
| Description | Character | 48 | Standard abbreviated description |
| Total | | 58 | |

Use:

This table can validate ICD codes.

Five years of codes will be kept.

Give a brief description of the code.

Show if the code is incomplete and in need of a fourth or fifth digit.

An ICD code which should have a 4th and/or 5th digit is listed with an "*".

This file interrelates with:
- Index Table
- Index Detail Table
- Index Global Table
- Qualifying Master Table
- Family Table
- All Parameter Tables Source:

ICD codes and description fields are purchased from HCFA (Health Care Financing Administration located in Baltimore, Md.).

The sub-code is maintained by the clinical staff.

Index Detail Table

This table groups ICD-9 codes into inclusive or exclusive diagnosis codes. This grouping is unique to each index code and is used to drive the search for each episode of care. ICD-9 codes have been classified into categories and given an indicator which determines whether or not the associated CPT code should be included in the episode of care. Also, an indicator may cause exclusion of any specific patient record from an episode of care summary analysis.

| | | | |
|---|---|---|---|
| ICD-9 | Alpha/Numeric or Character | 5 | Left justified assumed decimal after 3rd position. |
| Indicator | Character | 2 | I = Index code<br>R = Related<br>S = signs/symptoms<br>RO = Rule out<br>C = complications (exclude)<br>M = miscoded<br>V = Vcodes<br>MI = Miscoded Index |
| ICD-9 | Alpha/Numeric | 5 | ICD-9 Beginning Range Code |
| ICD-9 | Alpha/Numeric | 5 | ICD-9 Ending Range Code |
| Update | Character | 1 | A, C, or Blank |
| Total | | 17 | |

Use:

This table drives the search for the Episode of Care (EOC). Which is keyed off the Index Code.

Other codes to be included in the parameter search are specified in the indicator field. Any one of these ICD codes may or may not appear during the search for the Index code and still have the EOC be valid.

ICD codes with an indicator of "C" when found in a patient history will disqualify the entire patient from the EOC process.

Some Index codes are listed in part with "?" and "??" to exhibit that it does not matter what the trailing 4th and/or 5th digit is, the record is to be accessed for the parameter. For example, the Index code may be 701??, meaning that if the first three digits of the code start with 701 then use the regardless of what the 4th and/or 5th digit may be. This is true for all codes starting with 701.

ICD codes maintained in this table are listed as complete as verified by the ICD description table, with the exception of ICD codes with an indicator of "M". Programming logic should consider this when using "M" codes in the search process.

This file layout is used for drafting and populating a temporary file built from this table and the Index Global Table based on indicators and keys extrapolated from the Index table.

Program Logic to Assign Episode of Care

Any patient history with an ICD from the temp file for the chosen Index code is tagged for possible assignment of Episode of Care.

Perform a search on patient history for any ICD code from temp file with an indicator of "C". If found, exclude entire patient history from EOC search.

The qualifying tables are accessed to verify if specific qualifying factors apply to determine if patient history meets criteria for determination of valid episode of care. (See Qualifying Tables for further explanation)

The qualifying table is then accessed for further delineation of qualifying circumstances by EOC.

A timeline is tracked, by patient, for all potential Episodes of care that may occur for a given patient history.

The data is arrayed based on profile classes which are eight subsets of Procedure categories. An aggregate of all procedures can also be reported. (See Category Table for further explanation)

This table interrelates with:
- ICD Description Table
- Index Table
- Index Global Table
- Parameter Table
- CPT Statistic Table
- Age/Sex Table Source:

This table is generated and maintained by the Medicode staff.

Index Table

This table provides a preliminary filter for assigning and accessing different tables during the Episode of Care process. This table houses the assignment of staging and whether or not the Index Global table should be accessed.

| | | | |
|---|---|---|---|
| ICD-9 | Alpha/Numeric | 5 | Left justified assumed decimal after 3rd position. |
| Staging | Character | 2 | P = preventive<br>A = acute<br>C = chronic<br>L = life threatening<br>M = manifestations |

-continued

| | | | |
|---|---|---|---|
| Global Key | Alpha | 2 | C = complications |
| | | | M1 = miscoded medical vcodes |
| | | | M2 = miscoded surgical vcodes |
| | | | 1 = medical vcodes |
| | | | 2 = surgical vcodes |
| Indicator | Character | 2 | C = complications |
| | | | V = vcodes |
| Update | Character | 1 | A, C, or Blank |
| Total | | 12 | |

Use:

This table is used as a preliminary sort for Index codes before the EOC search.

Once an Index code has been selected, this table is searched for whether or not the global index table needs to be accessed.

This table assigns the staging for the index code which points to the window table.

This table interrelates with:
 ICD Description Table
 Index Detail Table
 Index Global Table
 Window Table Source:

This table is generated and maintained by the Medicode staff.

Index Global Table

This table gives a listing of ICD-9 codes common to most Index codes for either inclusion such as preventive or aftercare, or exclusion such as medical complications.

| | | | |
|---|---|---|---|
| GLOBAL KEY | Alpha/Numeric | 2 | C = complications |
| | | | M1 = miscoded medical vcodes |
| | | | M2 = miscoded surgical vcodes |
| | | | 1 = medical vcodes |
| | | | 2 = surgical vcodes |
| ICD Beginning | Alpha/Numeric | 5 | ICD-9 Beginning range code |
| ICD Ending | Alpha/Numeric | 5 | ICD-9 Ending range code |
| Update | Character | 1 | A, C, or Blank |
| Total | | 13 | |

USE:

This table is used to identify a generic V Code or complication ICD code to be used in an EOC search for any Index code.

It is triggered by the Index table.

The surgical Vcodes include all M1, M2, 1 and 2's.

Medical Vcodes include M1 and 1.

A complication ICD code will negate the use of a patient from the EOC search.

A temporary file for the index code is created based on ICDs extrapolated from this table as well as the Index detail table This table interrelates with:
 ICD Description Table
 Index Table
 Index Detail Table Source:

This table is generated and maintained by the Medicode staff.

Window Table

This table contains the number of days preceding and following an episode of care that must be present without any services provided to the patient relating to the index code or associated codes. These windows are used to define the beginning and end points of an episode of care. This table is driven from the staging field in the index table.

| | | | |
|---|---|---|---|
| Staging Indicator | Character | 2 | P = Preventive |
| | | | C = Chronic, A = Acute |
| | | | L = Life threatening, |
| | | | M = Manifestation |
| Beginning Window | Numeric | 3 | Number of days for no occurrence of ICD for Index Code |
| Ending Window | Numeric | 3 | Number of days for no occurrence of ICD for Index Code |
| Update | Character | 1 | A, C, or Blank |
| Total | | 9 | |

Use:

This table is keyed off of the staging and it tells the program how long of a "Clear Window" is needed on both ends of this EOC for it to be valid.

Source: This table is generated and maintained by the PP staff.

Procedure Parameter Table

This table contains the specific CPT codes identified for each index code listed chronologically with associated percentiles, mode, and average. The end user may populate an identical table with their own unique profiles created by analyzing their claims history data.

| | | | |
|---|---|---|---|
| ICD-9 Code | Alpha/Numeric | 5 | Left justified assumed decimal after 3rd position. |
| Profile | Alpha/Numeric | 2 | Mnemonic |
| Procedure | Alpha/Numeric | 5 | CPT, HCPCS |
| timeframe | Alpha/Numeric | 3 | Mnemonic for timeframe or total |
| 50th percentile | Numeric | 4 | Beginning percentile range |
| 50th percentile | Numeric | 4 | ending percentile range |
| 75th percentile | Numeric | 4 | beginning percentile range |
| 75th percentile | Numeric | 4 | ending percentile range |
| 95th percentile | Numeric | 4 | beginning percentile range |
| 95th percentile | Numeric | 4 | ending percentile range |
| Mode | Numeric | 3 | Numeric Count |
| Count | Numeric | 7 | Number of EOCs for timeframe |
| Sum | Numeric | 7 | Number of services for timeframe |
| Weighting | Numeric | 6 | Numeric count, assumed decimal (4.2) |
| Update | Character | 1 | A, C, or Blank |
| Total | | 63 | |

Use:

This table shows which CPT's are statistically and historically billed and how often based on an index ICD code.

It is keyed off of the index code and the category.

Source:

All of the field elements are obtained from the Procedure Detail Report.

Weighting is to be addressed in Phase II of the product.

Category Parameter Table

This table contains a listing of the categories identified for each index code listed chronologically with associated percentiles, mode, and average. The end user may populate an identical table with their own unique profiles created by analyzing their claims history data.

| | | | |
|---|---|---|---|
| ICD-9 Code | Alpha/Numeric | 5 | Left justified assumed decimal after 3rd position. |
| Profile | Alpha/Numeric | 2 | Mnemonic |
| Category | Alpha/Numeric | 4 | category |
| timeframe | Alpha/Numeric | 3 | Mnemonic of timeframe or total |
| 50th percentile | Numeric | 4 | beginning percentile range |
| 50th percentile | Numeric | 4 | ending percentile range |
| 75th percentile | Numeric | 4 | beginning percentile range |
| 75th percentile | Numeric | 4 | ending percentile range |
| 95th percentile | Numeric | 4 | beginning percentile range |
| 95th percentile | Numeric | 4 | and ending percentile range |
| Mode | Numeric | 3 | Numeric Count, assumed decimal (4.2) |
| Count | Numeric | 7 | Number of EOCs for the timeframe |
| Sum | Numeric | 7 | Number of services for the timeframe |
| Update | Character | 1 | A, C, or Blank |
| Total | | 56 | |

Use:
This table shows which categories are statistically and historically billed and how often based on an index ICD code. It is keyed off of the index code and the category.

Source:
All of the field elements are obtained from the Parameter Timeframe report.

Duration Parameter Table
This table contains the length of time associated with an episode of care for a given Index code. NOTE: The end user may populate an identical table with their own unique profiles created by analyzing their claims history data.

| | | | |
|---|---|---|---|
| ICD-9 | Alpha/Numeric | 5 | Left justified assumed decimal after 3rd position. |
| Profile | Alpha/Numeric | 2 | Mnemonic |
| 50th percentile | Numeric | 4 | beginning range |
| 50th percentile | Numeric | 4 | ending range |
| 75th percentile | Numeric | 4 | beginning range |
| 75th percentile | Numeric | 4 | ending range |
| 95th percentile | Numeric | 4 | beginning range |
| 95th percentile | Numeric | 4 | ending range |
| Mode | Numeric | 3 | beginning and ending range |
| Update | Character | 2 | A = Add C = Change |
| Total | | 36 | |

Use:
This table stores the projected length of an episode of care for a given index code.
It interrelates with:
  Index Detail table
  Parameter table
It is populated from the statistical analysis for each Index code.

Category Table
This table provides a grouping of CPT codes into categories of similar services.

| | | | |
|---|---|---|---|
| Category | Alpha/Numeric | 4 | Mnemonics |
| CPT | Alpha/Numeric | 5 | Beginning CPT Range |
| CPT | Alpha/Numeric | 5 | Ending CPT Range |
| Update | Character | 1 | A, C, or Blank |
| Total | | 15 | |

Use:
Procedure codes have been categorized according to most likely type of service they may represent. It could be characterized as a sorting mechanism for procedure codes.
The mnemonic used for this category is as follows:

$E_1$=Major E and M $E_2$=Minor E and M $L_1$=Major Laboratory $L_2$=Minor Laboratory $R_{D1}$=Major Diagnostic Radiology $R_{D2}$=Minor Diagnostic Radiology $R_{T1}$=Major Therapeutic Radiology $R_{T2}$=Minor Therapeutic Radiology $O_1$=Major Oncology Radiology $O_2$=Minor Oncology Radiology $M_{D1}$=Major Diagnostic Medicine $M_{D2}$=Minor Diagnostic Medicine $M_{T1}$=Major Therapeutic Medicine $M_{T2}$=Minor Diagnostic Medicine $S_{D1}$=Major Diagnostic Surgery $S_{D2}$=Minor Diagnostic Surgery $S_{T1}$=Major Therapeutic Surgery $S_{T2}$=Minor Therapeutic Surgery $A_1$=Major Anesthesia $A_2$=Minor Anesthesia $P_1$=Pathology J=Adjunct Categories are also used for arraying Episodes of Care into profile classes or can be reported as an aggregate. The subsets of the aggregate are:
0 Common Profile-$A_1$, $A_2$, $P_1$, $E_1$, $E_2$, $L_1$, $L_2$, $R_{D1}$, $R_{D2}$, $M_{D1}$, $M_{D2}$, $S_{D1}$, $S_{D2}$. (All of these categories are included as part of the other seven profile classes.
1 Surgery/Radiation/Medicine Profile—All Categories
2 Medicine/Radiation Profile—$M_{T1}$, $M_{T2}$, $R_{T1}$, $R_{T2}$, $O_1$, $O_2$
3 Surgery/Radiation Profile—$S_{T1}$, $S_{T2}$, $R_{T1}$, $R_{T2}$, $O_1$, $O_2$
4 Surgery/Medicine Profile—$S_{T1}$, $S_{T2}$, $M_1$, $M_{T2}$
5 Radiation Profile—$R_{T1}$, $R_{T2}$, $O_1$, $O_2$
6 Medicine Profile—$M_{T1}$, $M_{T2}$
7 Surgery Profile—$S_{T1}$, $S_{T2}$
This table interrelates with:
  Parameter Table
  Qualifying Tables
  Procedure Table Source:
Maintained by the clinical staff Qualifying Master Table
This table provides a preliminary filter for determining qualifying circumstances that may eliminate a patient history for determination of an Episode of Care. It also provides the initial sort of an episode of care for a specific profile class.

| | | | |
|---|---|---|---|
| Index Code | Alpha/Numeric | 5 | Left justified, assumed decimal after 3rd position |
| Scope | Alpha | 1 | P = Patient E = Episode of Care B = Both |
| Profile | Alpha/Numeric | 2 | Mnemonic or Blank |
| Group | Alpha/Numeric | 5 | Correlates to group ID in Qualifying Group Table |
| Update | Character | 1 | A, C, or Blank |
| Total | | 14 | |

Use:
Preliminary select for where in EOC process qualifying circumstances should apply.
This table interrelates with:
  Index Detail Table
  Qualifying Group Table
Logic:
The Qualifying Master Table outlines the Index code, where in the data search the qualifying search is to occur and what qualifying groups are associated with the index code. The locations include P=patient search, E=Episode of Care search, or B=search in both.
The Profile field is numbered based on the 8 different profiles outlined under the category table. If blank, a profile is not relevant. They are as follows:
0. Common Profile
1. Surgery/Medicine/Radiation Profile
2. Medicine/Radiation Profile
3. Surgery/Radiation Profile
4. Surgery/Medicine Profile
5. Radiation Profile
6. Medicine Profile
7. Surgery Profile
The Group field assigns a 5 byte mnemonic that establishes a set of qualifying rule sets for a given index code. This field keys directly to the Qualifying Group Table. The majority of the groups relate to profile classes. They are as follows:
ALL (Surgery/Medicine/Radiation Profile)
MRPRO (Medicine/Radiation Profile)
SRPRO (Surgery/Radiation Profile)
SMPRO (Surgery/Medicine Profile)
RPRO (Radiation Profile)
MPRO (Medicine Profile)
SPRO (Surgery Profile)
CPRO (Common Profile)
There are 3 other groups which establish a set of qualifying circumstances based on the occurrence of a particular procedure or diagnosis. These are as follows:
SURG Certain Index codes are commonly associated with an invasive procedure which should be present during the course of treatment.
MED Certain Index codes are commonly associated with an E/M service which should be present during the course of treatment.
ONLY The Index code must occur at least twice on different dates of service over the course of treatment. This group looks only for this occurrence. No specific procedure is to be sought in conjunction with the Index code.
Source:
Table maintained by Clinical staff.

Qualifying Group Table
Table groups certain qualifying circumstances to aid in an efficient search for data meeting the criteria.

| Group | Alpha/Numeric | 5 | Left justified assumed decimal after 3rd position |
|---|---|---|---|
| Rule Type | Alpha/Numeric | 2 | II = Index Code specific rule<br>IS = specific ICD code rule<br>IC = multiple ICD to category rule<br>CC = Multiple code rule<br>CS = code specific rule<br>IG = ICD to gender rule<br>IA = ICD to age rule |
| Rule Identifier | Alpha/Numeric | 1 | T = True F = False (toggle)<br>M = Male F = Female if IG rule type |
| Number required | numeric | 2 | number value |
| Update | Character | 1 | A, C, or Blank |
| Total | | 15 | |

Use:
To act as a preliminary qualifying mechanism for determining if claims information can be used in the assignment of a parameter.
This table interrelates with:
  Qualifying Index Table
  Qualifying Code Table
  Qualifying Master Table
A rule type (or rule types) is assigned by group delineating if the rule applies to a single or multiple ICD, single or multiple CPT or category or any combination thereof.
The rule identifier is an assigned mnemonic based on what the rule is to achieve.
The Logical indicates if the rule is positive or negative (inclusionary or exclusionary)
The number required is a count of the number of occurrences for the rule to be valid.

Logic:
The Group Id is driven by the groups assigned in the Qualifying master table. All qualifying rule sets assigned to a given group should be performed to determine the qualifying circumstances for a given index code. See Qualifying Master Table for an explanation of each group.
The Rule Type is a mnemonic which assigns a common type of logic that is to be implemented in the search for the qualifying circumstances. It is possible that the same rule type could be associated with many different rule identifiers. The rule type will also point to either the Qualifying Index Table or the Qualifying Code Table as determined by the first byte of the filed. The following is a listing of the rule types:
Rule Types Associated with Qualifying Index Table:
II This related directly to the Index code only.
IC This rule is for any indicated ICD code associated with the Index code as it relates to a category or procedure.
IS This rule is for a specific indicated ICD code associated with the Index code as it relates to a category or procedure.
IG This rule is for any indicated ICD code associated with the Index code as it relates to age. The age ranges to be used are:
  0-1=newborn/infant
  1-4=early childhood
  5-11=late childhood
  12-17=adolescence
  18-40=early adult
  41-64=late adult
  65-99=geriatric
  12-50=female childbearing age
Rule Types Associated with Qualifying Code Table:
(Additional rule types may be added when necessary for phase II of the product.)
CC This rule is for a specific procedure or category as it relates to another specific procedure or category for any ICD code associated with the Index code.
CS This is for a specific procedure or category as it relates to a specific ICD code associated with the Index code.

The Rule Identifier is a further break out of the qualifying circumstances for a group. Most of the rule Ids relate directly to components of a given profile to be included or excluded. For example the rule ID of MMR relates directly to the group of MRPRO and delineates that the further breakout is for Radiation.

The other 3 major rule Ids relate directly to the remaining 3 groups. These are:

| Group | Rule ID |
|---|---|
| ONLY | O |
| SURG | S |
| MED | M |

The logical is a toggle for whether the rule is true or false. If the rule type is IG, the toggle is for Male or Female.

The number required is a count for the minimum occurrence that the qualifying circumstance can occur.

Source:
To be maintained by clinical staff

Qualifying Index Table
Table houses common qualifying circumstances based on presence or non-existence of given procedures and/or ICD codes that would qualify or disqualify a patient history in the determination of an Episode of Care.

| | | | |
|---|---|---|---|
| Rule Type | Alpha/Numeric | 2 | II = Index Code specific rule<br>IS = specific ICD code rule<br>IC = multiple ICD to category rule<br>IA = ICD to age rule<br>EG = ICD to gender |
| Rule Identifier | Alpha/Numeric | 4 | assigned from Qualifying Master Table |
| Indicator | Alpha/Numeric | 2 | I = Index code<br>R = Related<br>S = signs/symptoms<br>RO = Rule out<br>M = miscoded<br>V = Vcodes<br>MI = Miscoded Index<br>or Blank |
| Code | Alpha/Numeric | 5 | category, CPT, HCPCS, ICD or blank |
| Update | Character | 1 | A, C, or Blank |
| Total | | 14 | |

Use:
To act as a qualifying mechanism for determining if claims information can be used in the assignment of a parameter
This table interrelates with:
  Procedure Table
  Category Table
  Qualifying Group Table
  ICD Description Table
  Index Detail Table
All rules generated from this table deal with an ICD code driven by the indicator, regardless of the Index code. If the rule is ICD only, then the procedure is blank. If the rule is ICD and procedure, then the indicated ICD must correlate with a procedure code or category.
If the indicator is blank, then all indicators should be considered for qualifying circumstances. Listing a specific indicator causes a qualifying search on the associated indicator only.

Logic:
The first two fields of the Qualifying Index Table reiterates the rule type and rule identifier as outlined in the Qualifying Group table. Both of these fields are key.
The indicator correlates to the indicators in the Index Detail table. If the field is blank, all ICDs for the index code should be sought for the rule.
The code filed could be a CPT, HCPCS, category or ICD code. If this field is blank, no specific code or category should be sought for the rule.

Source:
To be maintained by clinical staff

Qualifying Code Table
Table houses common qualifying circumstances based on the presence or non-existence of a given combination of procedure codes that would qualify or disqualify a patient history in the determination of an Episode of Care.

| | | | |
|---|---|---|---|
| Rule Type | Alpha/Numeric | 2 | CC = Multiple code rule<br>CS = code specific rule |
| Rule Identifier | Alpha/Numeric | 4 | As labeled in Qualifying Master Table |
| Primary code | Alpha/Numeric | 5 | CPT, HCPCS or category or ICD |
| Secondary Code | Alpha/Numeric | 5 | CPT, HCPCS or category or ICD |
| Update | Character | 1 | A, C, or Blank |
| Total | | 14 | |

Use:
To act as a qualifying mechanism for determining if claims information can be used in the assignment of a parameter.
This table interrelates with:
  Procedure Table
  Category Table
  Qualifying Group Table
All rules generated from this table have to do with a procedure or category driven by the qualifying master table. The rule relates to the procedure or category as listed in the primary and secondary fields.

Logic:
The first two fields of the Qualifying Index Table reiterates the rule type and rule identifier as outlined in the Qualifying Group table. Both of these fields are key.
The Primary code is the driving code in the rule search for the qualifying circumstance. It can be a CPT, HCPCS, category or ICD code.
The Secondary code is the code that must be associated with the primary code in the rule search for the qualifying circumstance. It can be a CPT, HCPCS, category or ICD code.

Source:
To be maintained by clinical staff.

Specialty Table
Table provides a listing of medical specialties with an assigned numeric identifier. This is standard HCFA information.

| | | | |
|---|---|---|---|
| Specialty (Key) | Alpha/Numeric | 3 | Medicare specialty indicator |
| CPT | Alpha/Numeric | 5 | Beginning CPT to include |
| CPT | Alpha/Numeric | 5 | Ending CPT to include |
| Update | Character | 1 | A, C. or Blank |
| Total | | 14 | |

Use:
This table is used to specify which Specialty is most commonly used with which CPT.
A description of the specialty will be in the documentation.

Source:
This table will be taken from the list Med-Index Publications maintains (available from Medicode, Inc. located in Salt Lake City, Utah).

Zip/Region Table
Table provides a listing of geographical zip codes sorted into 10 regional zones, standard HCFA information.

| Region Indicator | Alpha/Numeric | 2 | Medicares Ten Regions |
|---|---|---|---|
| Zip Code | Numeric | 5 | Beginning Zip Code Range |
| Zip Code | Numeric | 5 | Ending Zip Code Range |
| Update | Character | 1 | A, C, or Blank |
| Total | | 13 | |

Use:
This table is used to specify which Medicare Region to use for the statistic table.

Source:
This will be generated by Medicode, Inc. staff.

Specialty Statistic Table
Table provides a listing of medical specialties with an assigned numeric identifier. This is standard HCFA information.

| ICD-9 Code | Alpha/Numeric | 5 | Left justified assumed decimal after 3rd position. |
|---|---|---|---|
| Specialty | Alpha/Numeric | 3 | |
| CPT Code | Alpha/Numeric | 5 | Beginning Range (Service Area) |
| CPT Code | Alpha/Numeric | 5 | Ending Range (Service Area) |
| Category | Alpha/Numeric | 4 | Mnemonic |
| Multiplier | Numeric | 6 | Implied decimal (4.2) |
| Update | Character | 1 | A, C, or Blank |
| Total | | 29 | |

Use:
This table is a matrix that is directly tied to the parameter table by the index code. Its purpose is to give a numeric multiplier that is applied to the occurrence field in the parameter table, to vary the parameter by service area and/or sex and/or region. (i.e., if the occurrence is 2 and the multiplier for a specialist is 1.5, the specialist may receive a total of 3.)
If multiple multipliers are used, compute the average of them and use that.

Source:
This table will be generated by the computer using the extended data set, and validated clinically by the clinical staff.

Age/Gender Statistic Table
Table provides a listing of each CPT code for an index code with a numerical factor used to adjust the frequency of each code by age and/or gender specific data analysis.

| ICD-9 Code | Alpha/Numeric | 5 | Left justified assumed decimal after 3rd position. |
|---|---|---|---|
| Age | Alpha/Numeric | 2 | 00-99 |
| Sex | Alpha/Numeric | 1 | M, F or Blank |
| Category | Alpha/Numeric | 3 | Mnemonic |
| Multiplier | Decimal | 6 | Implied decimal (4.2) |
| Update | Character | 1 | A, C, or Blank |
| Total | | 18 | |

Use:
This table is a matrix that is directly tied to the parameter table by the index code. Its purpose is to give a numeric multiplier that is applied to the occurrence field in the parameter table, to vary the parameter by service area and/or sex and/or region. (i.e. if the occurrence is 2 and the multiplier for a male is 1.5, the male may receive a total of 3.)
It multipliers are used, compute the average of them and use that.

Source:
This table will be generated by the computer using the extended data set, and validated clinically by the clinical staff.

Region Statistic Table
Table provides a listing of CPT code for an index code with a numerical factor used to adjust the frequency of each code by regional data analysis.

| ICD-9 Code | Alpha/Numeric | 5 | Left justified assumed decimal after 3rd position. |
|---|---|---|---|
| Region | Alpha/Numeric | 2 | Medicares Ten Regions |
| Multiplier | Decimal | 6 | Implied decimal (4.2) |
| Update | Character | 1 | A, C, or Blank |
| Total | | 14 | |

Use:
This table is a matrix that is directly tied to the parameter table by the index code. Its purpose is to give a numeric multiplier that is applied to the occurrence field in the parameter table, to vary the parameter by service area and/or sex and/or region. (i.e., if the occurrence is 2 and the multiplier for a region is 1.5, the region may receive a total of 3.)
If multiple multipliers are used, compute the average of them and use that.

Source:
This table will be generated by the computer using the extended data set, and validated clinically by the clinical staff.

Family Table
Table provides a listing of ICD-9 codes which have been clustered into family groupings.

| Family Description | Character | 24 | Name of Family/Cluster |
|---|---|---|---|
| ICD-9 Code | Alpha/Numeric | 5 | Beginning ICD-9 Range |
| ICD-9 | Alpha/Numeric | 5 | Ending ICD-9 Range |
| Total | | 34 | |

Use:
This table is used for in-house purposes only. It provides a listing of a ICD Family/Cluster with a description of the Family/Cluster.

Source:
This table is generated and maintained by the clinical staff.

File Layout for Claims Data Contribution

We prefer Electronic Media Claims National Standard Format; however, if you are not using EMC the following is our suggested layout. Please include an exact layout of the format you use with your submission. The record layout that follows is for each line item that appears on a claim. The charge (field 19) should be the non-discounted fee-for-service. There should be no aggregation or fragmentation.

| Field Number | Description | Length | Alpha/ Numeric | Comments |
|---|---|---|---|---|
| 1. | Rendering Provider ID | 15 | A/N | Unique provider Identification number or SSN |
| 2. | Billing Provider ID | 16 | A/N | Unique provider Identification number or SSN |
| 3. | Provider Specialty | 3 | A/N | Supply a List of Specialty codes used |
| 4. | Patient ID | 17 | A/N | Unique patient ID number or SSN. May be an encrypted of encoded format. |
| 5. | DOB | 6 | N | Patient Date of Birth MMDDYY |
| 6. | Sex | 1 | A | M = Male, F = Female |
| 7. | Subscriber ID | 25 | A/N | Insured's I.D. No., Normally SSN |
| 8. | Relationship | 1 | N | Patient to Subscriber. 1 = Self, 2 = Spouse, 3 = Dependent |
| 9. | Bill ID | 15 | A/N | Unique claim/bill Identification number |
| 10. | From Date of Service | 6 | N | MMDDYY |
| 11. | To Date of Service | 6 | N | MMDDYY |
| 12. | Provider Zip | 5 | N | Standard 5 digit Zip Code |
| 13. | Place of Service | 2 | A/N | Supply a list of POS codes used |
| 14. | Type of Service | 2 | A/N | Supply a list of TOS codes used |
| 15. | Procedure Code | 5 | N | Submitted CPT or HCPC code |
| 18. | Modifier | 2 | N | Submitted CPT modifier |
| 17. | 2nd Modifier | 2 | N | If multiple modifiers are submitted, show the second modifier used. Anesthesia Modifiers (P1-P6) |
| 18. | Claim type | 3 | A/N | Payor Class Code-W/C, HCFA, Medicald etc. |
| 19. | Charge | 5 | N | Billed amount, right justified, whole dollars |
| 20. | Allowed Amount | 5 | N | Right justified, whole dollars |
| 21. | # of days/units | 5 | N | number of days and/or units |
| 22. | Anesthesia time | 3 | N | Actual Minutes |
| 23. | ICD1 | 5 | A/N | First diagnostic code attached to procedure |
| 24. | ICD2 | 5 | A/N | Second diagnostic code attached to procedure (Both ICD1 & ICD2 are left justified, assumed decimal after 3rd byte) |
| 25. | ICD3 | 5 | A/N | Third diagnostic code attached to procedure |
| 26. | ICD4 | 5 | A/N | Fourth diagnostic code attached to procedure |
| 27. | Out-patient facility | 5 | A/N | Outpatient facility/outpatient hospital Identifier |
| 28. | Revenue Code | 3 | N | Revenue center code |

Acceptable Media Types 9 track tape: 1600 or 6250 BPI, ASCII or EBCDIC, Labeled or Unlabeled, Unpacked data, Fixed record lengths Floppy disk; 3.5" (1.44 Mb or 720K) or 5.25" (1.2 Mb or 360K), Standard MS-DOS formatted disk, ASCII fixed record length or delimited file DC 600 A or DC 6150 cartridge: "TAR" or single ASCII or EBCDIC file, Unpacked data, Fixed record lengths 8 mm Exabyte tape: "TAR" or single ASCII or EBCDIC file, Unpacked data, Fixed record lengths 3480 cartridge: Unpacked data, Fixed record lengths, Compressed or Uncompressed Maximum Block size 64,280

This invention is a process for analyzing healthcare providers' billing patterns to assess utilization patterns of medical services. The method of the invention incorporates a set of statistically derived and clinically validated episode of care data to be used as a paradigm for analyzing and comparing providers' services for specific diagnoses or medical conditions. This invention utilizes a series of processes to analyze the client's healthcare claims history to create unique parameters. In its preferred embodiment, the invention is implemented in software. The invention provides the following functions or tools to the client: creation of local profiles, display of profiles and comparison of profiles.

The creation of local profiles function gives the client the ability to develop unique episode of care profiles utilizing their own claims history data. The process for creating these profiles is identical to the process used in the development of the reference profiles.

The display of profiles function provides a look-up capability for information stored in the reference tables or in client generated profiles tables. This look-up capability may be displayed on the computer screen or viewed as a hard-copy print out.

The comparison of profiles function provides a comparison between any two profile sources with attention to variance between them. This includes comparing client specific profiles to reference tables, comparing a specific subset of the client's data (eg, single provider) against either reference tables or the client's profiles, or comparing different subsets of the client's profiles to subsets of reference tables.

Figure 10:
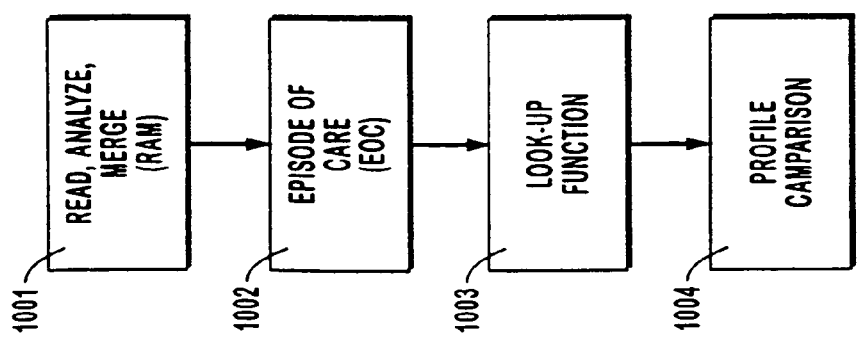
FIG. 10 depicts principle elements of the invention and their relationship to each other.

There are four main processes involved in the invention, as depicted in FIG. 10. These are Read, Analyze and Merge (RAM), 1001, further depicted in FIG. 11; Episode of Care analysis (EOC), 1002, further depicted in FIG. 12; Look-up function, 1003, further depicted in FIGS. 13 and 14; and Profile Comparison, 1004, further depicted in FIG. 15. The invention also includes an innovative reporting mechanism. Each of these four main processes and the reporting mechanism is described in detail in the remainder of this section.

A. Transforming Raw Data into an Informative Database

Both the RAM and the EOC processes involve healthcare claims history search and analysis. The intent of the RAM and the EOC claims history processing is to enable the end user to establish their own unique profiles based on their existing claims data information. Developing a database of historical provider billing data which will be used to provide the functionality of the invention is the first step in the invention.

1. Read, Analyze and Merge ("RAM")

In order to define a profile a significant quantity of historical medical provider billing information must be analyzed. As indicated above, the provider billings may come from a variety of sources, with the general guideline that accuracy and completeness of the data and a statistically significant sample of provider billings required to develop a reliable profile. In the preferred embodiment of the invention, no less than two years' of consecutive claims history and about fifty million claims are used to develop the profiles. The RAM process verifies existence and validity of all data elements in a claims history before the data is processed to develop a profile. The reader is directed to FIGS. 1 and 6-8 for pictorial representations of the preferred embodiment of the invention. FIG. 1 depicts the high level steps performed in one embodiment of the invention. The data flow shown in FIG. 1 includes loading client data 101 from tape 100, reordering various fields 103 and performing date of service expansion 104 as necessary. Next, data are merged (combined) 1-5 and sorted 106 to ensure all bill ID's are grouped together. The data 108 is then read, analyzed and merged into an extended data set (EDS) 110. Reporting and any other processing may occur 111 and an Episode of Care database 112 is created. The preferred embodiment of this invention. In the preferred embodiment of the invention, the steps of the invention are implemented in a software product referred to as CARE TRENDS available from Medicode, Inc. of Salt Lake City, Utah.

Figure 6:
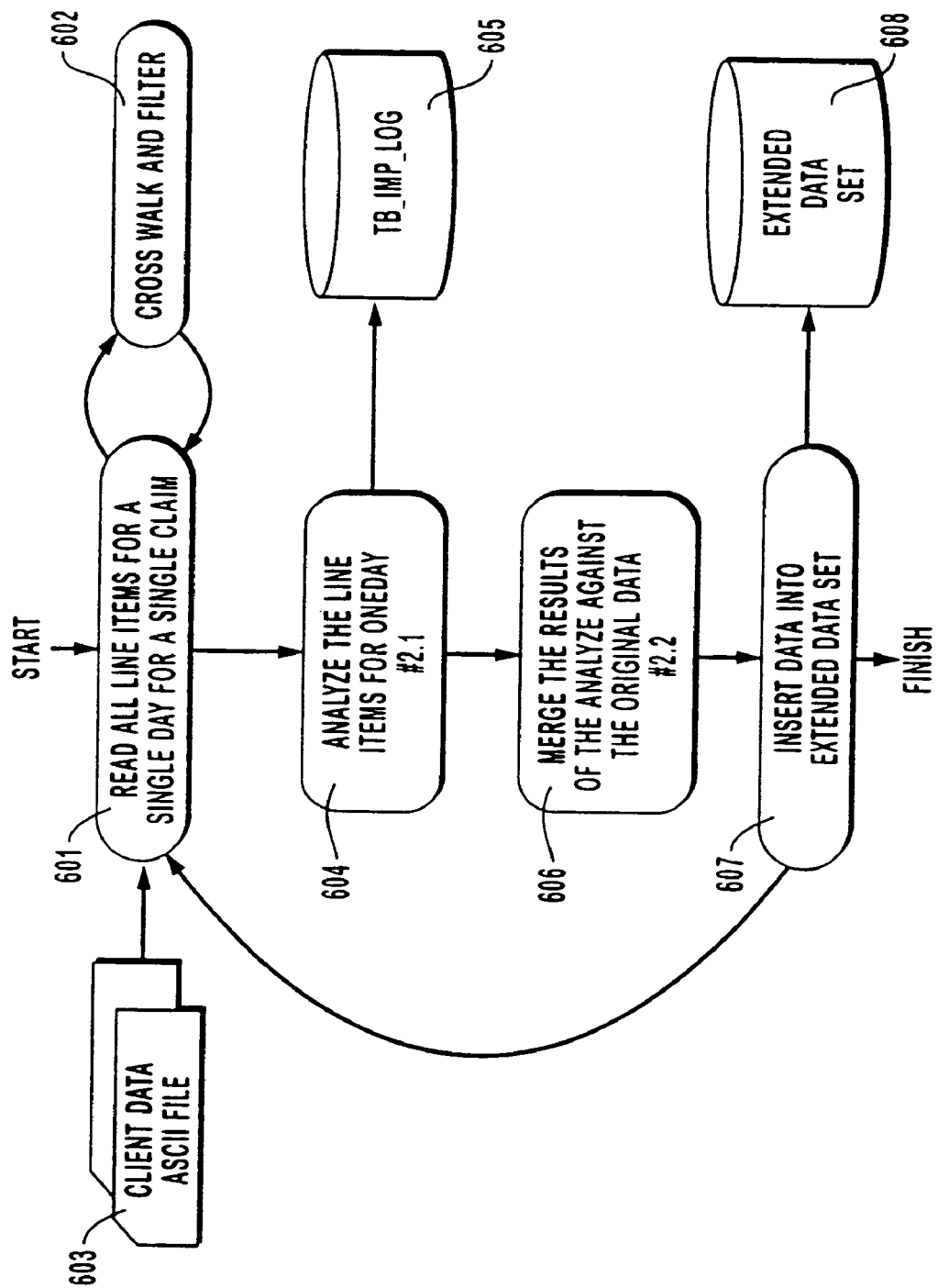
FIG. 6-8 depicts processing of data before episode of care processing begins.

FIG. 6 depicts read, analyze and merge processing that occurs in the preferred embodiment of the invention. First, one claim at a time the data 603 is read 601, cross walked and scrubbed (filtered) 602. Then a claim is analyzed 604 with result output to a log file 605. The results in the log file 605 are then compared 606 to the original claim data and inserted 607 into an extended data set 608.

Figure 7:
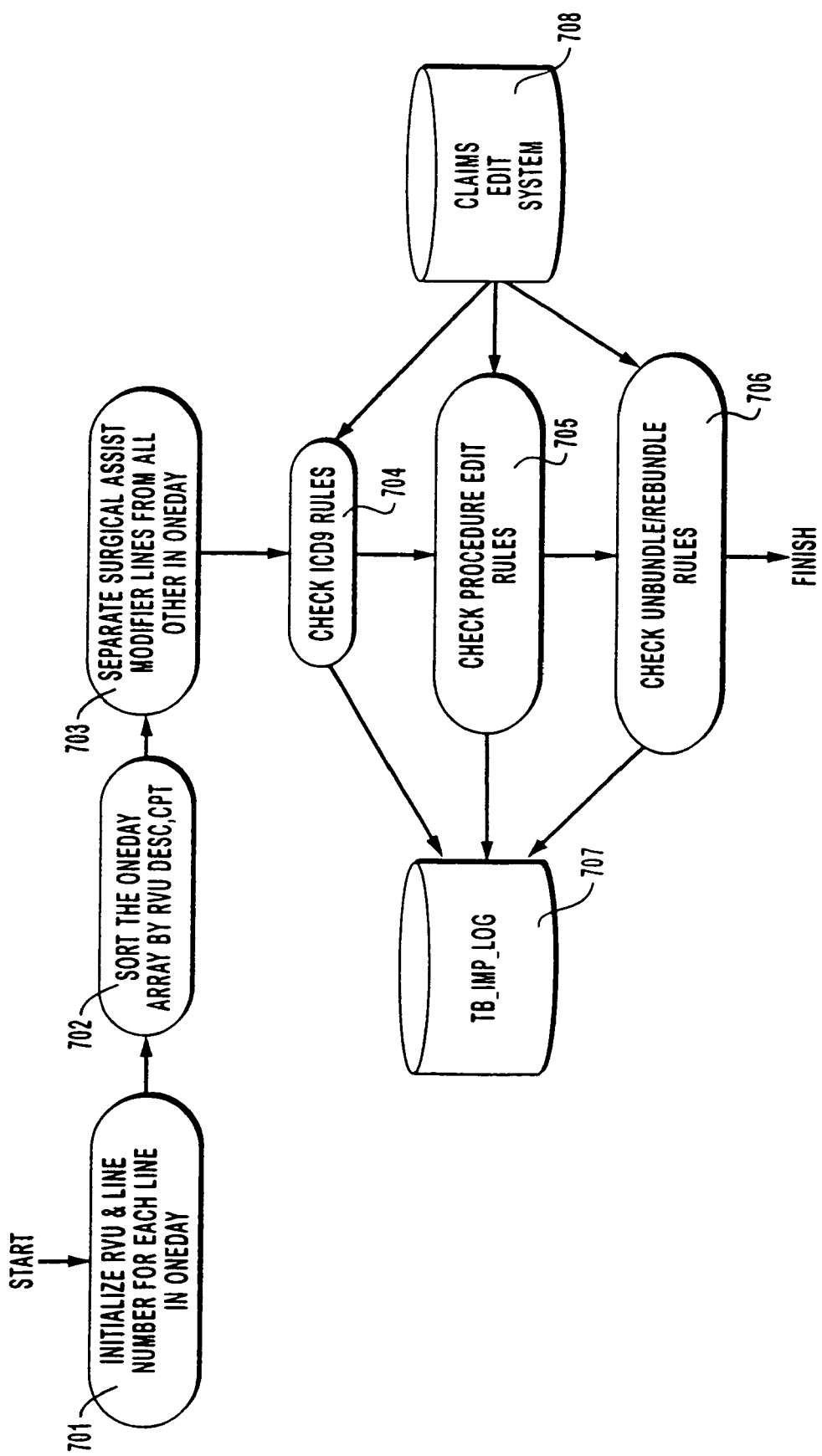

FIG. 7 depicts an analytical process of the preferred embodiment that includes initializing 701 RVU and line number for each line of the claim and sorting 702 by RVU (descending) and CPT and charge in order to prepare for proper analysis by CES. Then 703 line items are split into two groupings of surgical assistant modifiers and all other modifiers in separate groups. Each of the two groups is then checked 704 against disease classification codes (ICD 9), procedure edits rules 705 (CES tables) and unbundle/rebundle edits 706 are performed.

Figure 8:
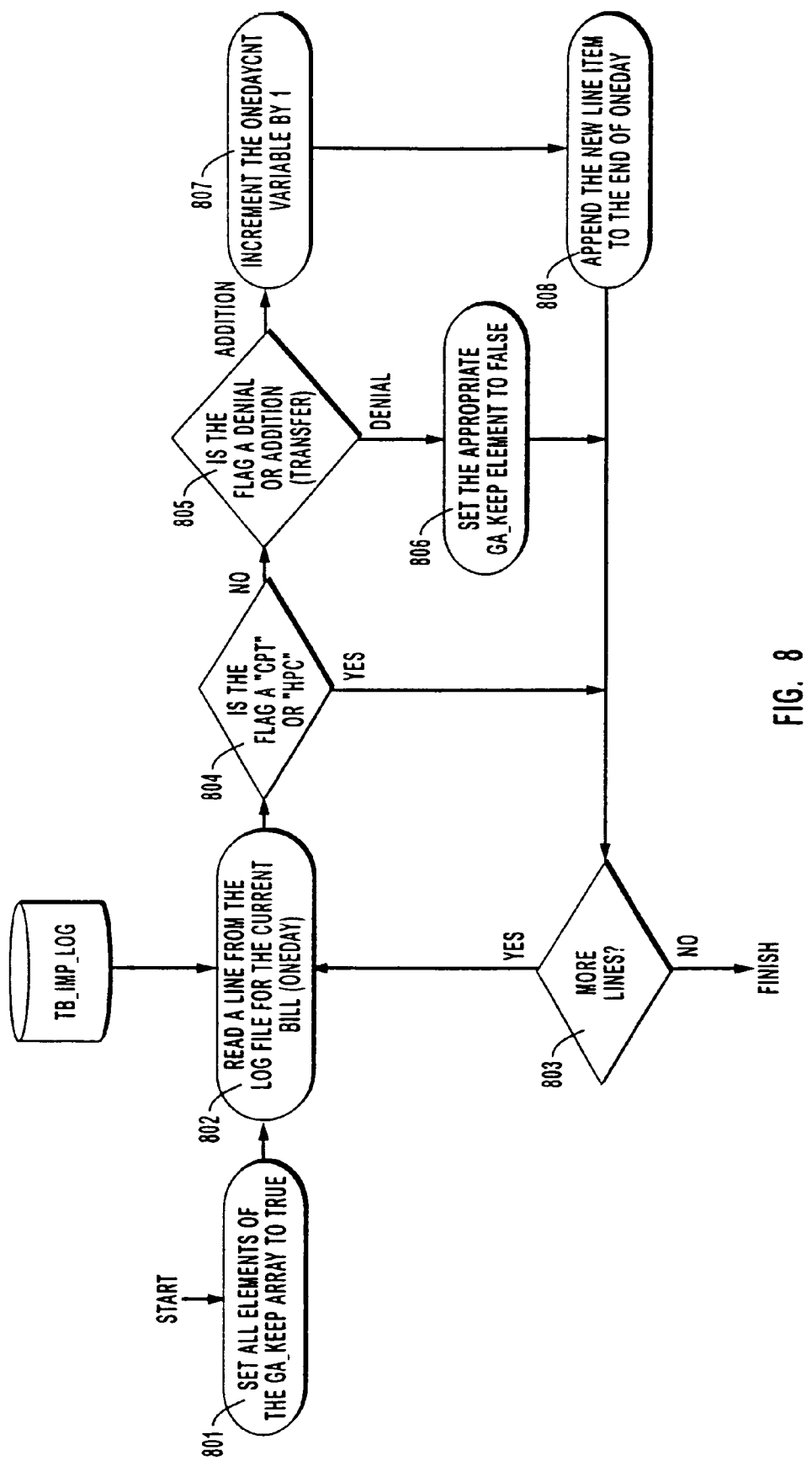

FIG. 8 depicts the merge process of the preferred embodiment of the invention. It includes reading 802 each line of from the log file for current bill, proceeding with processing if the record read is pertinent 804, determining whether to add the record to the extended data set 805-807, (i.e. not adding denials, adding rebundles and adding other lines that have not been specifically excluded).

Figure 9:
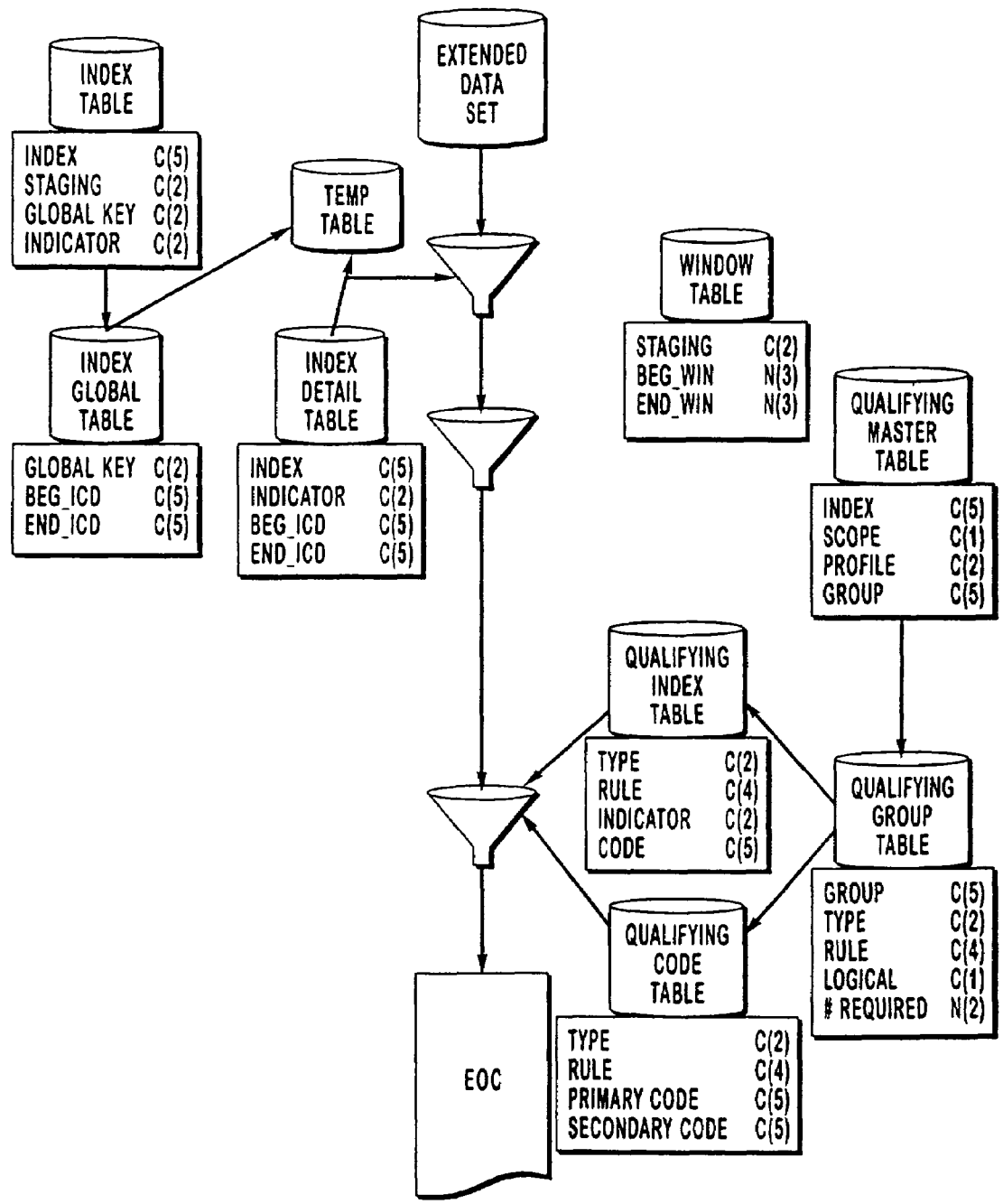
FIG. 9 depicts episode of care processing.

FIG. 9 depicts episode of care formation in the preferred embodiment. This processing includes processing the records in the extended data set that relate to the current index code. This relation is determined by the index tables. Then the records are broken into potential episodes of care based on a period of time specified in a window table. Then the episode of care is qualified based on the rules in a qualifying table. Qualifying episodes of care are inserted into the episode of care table.

Figure 11:
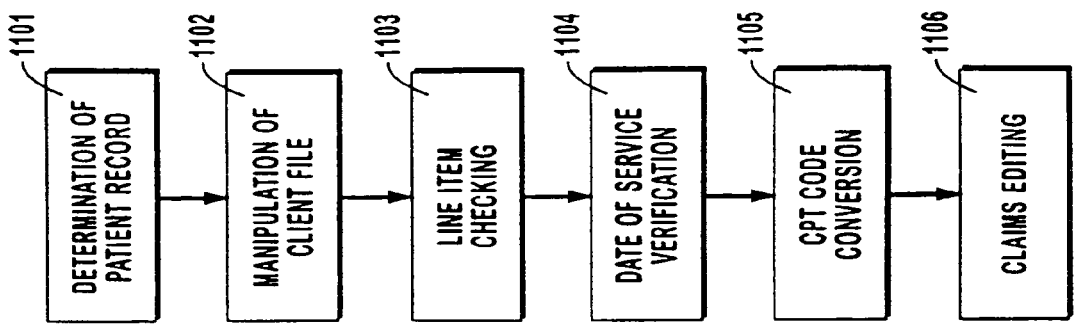
FIG. 11 depicts the process of the preferred embodiment of the Read, Analyze, Merge element of the invention.

The following text includes a written description of the RAM processing that is performed in the preferred embodiment of the invention. FIG. 11 shows the RAM process.

The first step in the RAM process is determination of a patient record, 1101. It is necessary to establish a patient record that can be used in the episode of care extraction process (explained in detail below). In the preferred embodiment, a patient record is identified as a unique patient history involving no less than two years of sequential claims history. Because identifying patient information is often removed from patient records to ensure patient confidentiality, patient information such as subscriber/relationship, patient ID, age, gender, bill ID and claim ID may be useful in positively identifying a particular patient. It should be noted that claims history data from various sources may need to be handled differently to identify patient records due to differences in file organization and level of detail of information provided. The amount of information desired to be captured may vary in different embodiments of the invention, but generally the information to be captured is that on a standard HCFA 1500 billing form, Electronic Media Claims, UB 82 or UB 92 claim forms, all of which are generally known in the industry.

The next step, 1102, is the manipulation of the client file layout to extrapolate or crosswalk the pertinent information in order to conform to the logic of the invention. Examples of this step include: translation of Type of Service or Benefits to Specialty type, modifiers, and/or place of service information.

The next steps involve the validation of claims elements. Each line item of claims history is compared against the Procedure, the Description table, (such as CPT or HCPCS description tables; HCPCS means Health Care Financing Administration Common Procedure Coding System provided by the U.S. Government; such tables generally are referred to as Description Tables and may contain any coding schemes) and the ICD description tables to validate the codes contained in the line item, 1103. Line items with an invalid code are not included in the remainder of RAM processing, though they are counted for future reference. Line items which indicate services being performed over a period of more than one day are expanded into numerous line items, one for each service performed, 1104. This function is also performed only on CPT codes 10000-99999. The services are then each given a unique date of service beginning with the "date of service from" for the first line item and ending with the "date of service to", for the last line item. The last validation step, 1105, is the conversion of old CPT codes to new CPT codes. This step is essential to provide the most accurate statistics relative to physician office and hospital visits (termed Evaluation and Management Services).

The last step of the RAM process is to edit all claims for errors, through an appropriate claims edit tool, 1106. In the preferred embodiment, software known as "CLAIMS EDIT SYSTEM" which is available from Medicode, Inc. located in Salt Lake City, Utah is used to detect and correct any duplicate line items or inappropriately billed services. This results in an appropriately processed set of raw data that is now in a condition for episode of care processing. The reader is directed to the RAM source code in the Microfiche Appendix for all details of this processing performed in the preferred embodiment.

2. Determination of Episode of Care

Figure 2:
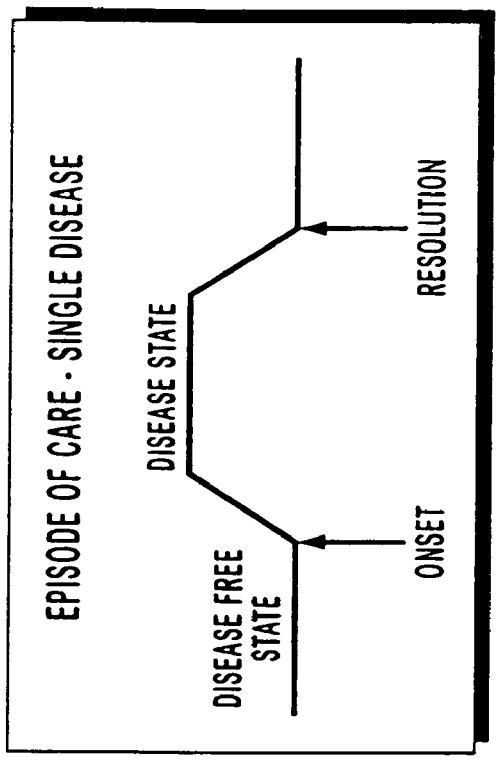
FIG. 2 depicts an episode of care for a single disease.

The next step in transporting raw data into a useful database is to determine episodes of care for the data that has already undergone RAM processing. In the invention, a database is created which contains profiles for various diagnoses, chronic and otherwise, including complications indicators. Creation of the database depends on accurately defining an episode of care ("EOC") for each diagnosis. An episode of care is generally considered to be all healthcare services provided to a patient for the diagnosis, treatment, and aftercare of a specific medical condition. The episode of care window for a single disease is depicted in FIG. 2. In the simplicity of the figure, it can be seen that for the diagnosis in question, all healthcare services provided between onset and resolution should be incorporated into the database. An example of this would be a patient who has been afflicted with acute appendicitis. The patient's life prior to onset of the acute appendicitis would be considered a disease free state. On some date, the patient would notice symptoms of acute appendicitis (although he may not know the diagnosis) that cause him to seek the attention of a medical provider. That event would be considered the onset. During the disease state, numerous events may occur, such as the patient consulting a family practitioner, consulting a surgeon, laboratory work and surgical services being performed, and follow-up visits with the provider(s). When further follow-up is no longer required, resolution has been reached. Thus an episode of care has been defined and data from that patient's episode of care is used in the invention to construct a profile for the diagnosis applicable to that patient. Without the use of additional logic, however, the use of that definition of an episode of care would result in erroneous data being entered into the profile database.

Figure 3:
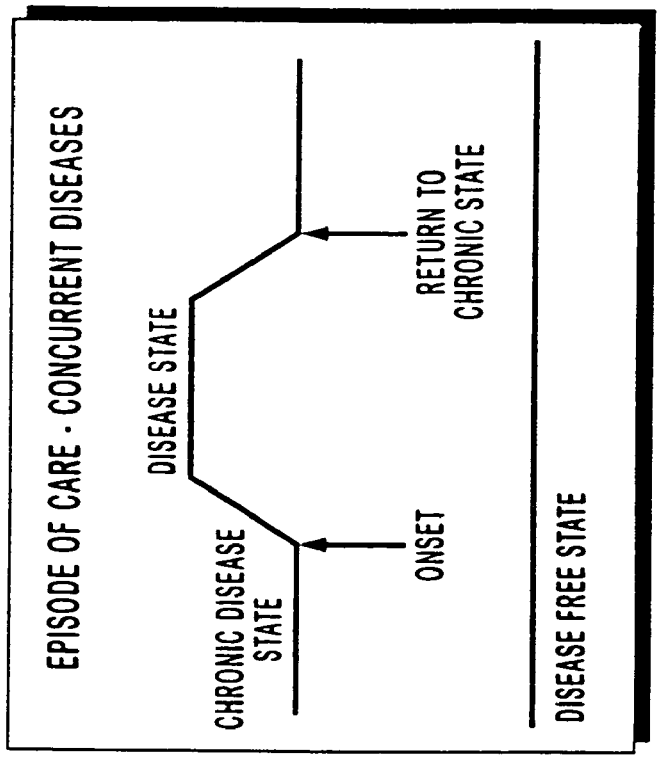
FIG. 3 depicts an episode of care for concurrent diseases.

For example, in FIG. 3 it can be seen that a patient suffering from a chronic disease who contracts a second disease could be treated both for the chronic disease and for the second disease during the disease state (i.e. between onset and resolution). If all medical provider billing data during the disease state were entered into the database, then the database would contain erroneous historical data for that individual's diagnosis. For example, if a patient who suffers from psoriasis were to be diagnosed with acute appendicitis and received treatment for psoriasis between the time of onset and resolution of his acute appendicitis, then the provider billings would contain both billings for treatment of the psoriasis and the acute appendicitis. Therefore the invention incorporates methods for discerning medical provider billings irrelevant to a particular diagnosis. Further, the disease state could be the active state of a chronic disease, and resolution could be the disease returning to its inactive state. A method for handling this situation is therefore also provided.

Figure 4:
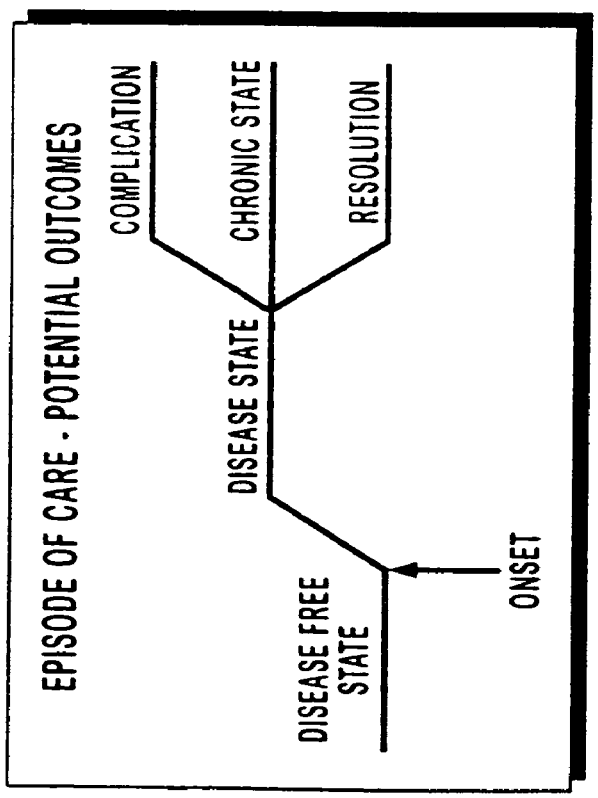
FIG. 4 depicts potential outcomes for an episode of care.

Other alternatives in the course of a disease further complicate accurately defining an episode of care. From FIG. 4 it can be seen that for any particular diagnosis, the outcome could be resolution, as described above, return to the chronic state of a disease, or complication of the disease. For example, if a patient has undergone an appendectomy, the patient may contract an infection following the surgical procedure. Because complications of various types and durations and in varying frequencies are associated with various diagnoses, a method for incorporating the complication data into the statistically-derived practice parameter is intended to be provided in the invention.

Figure 5:
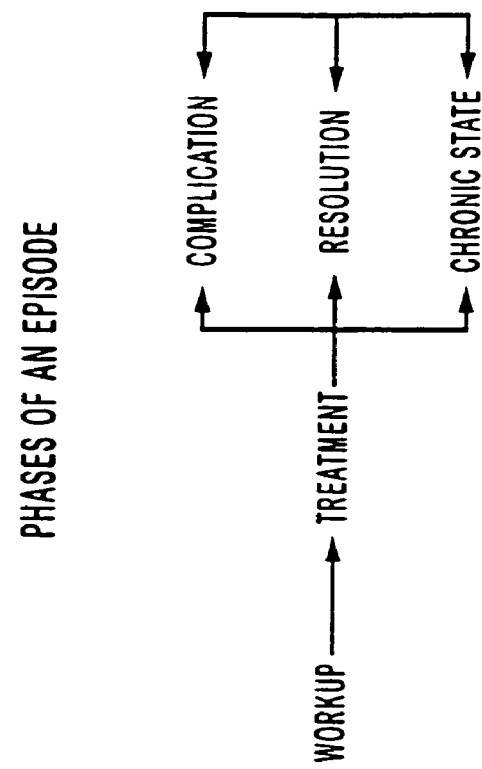
FIG. 5 depicts phases of an episode of care.

FIG. 5 depicts the phases of an episode of care, including the sequence of patient workup, treatment, and eventual resolution, return to the chronic state, or complication followed by either resolution or return to the chronic state.

The method for defining an entire episode of care provided in the invention is used to construct a database of profiles based on billing data that has been filtered to eliminate data irrelevant to the diagnosis which would lead to an erroneous profile. Essential to the determination of an EOC are certain qualifying circumstances. These circumstances are managed through the use of four inter-relational qualifying tables, to provide a mechanism for sorting patient history for the occurrence of specific procedures or ICD codes that are requisite for an EOC to be valid.

Figure 12:
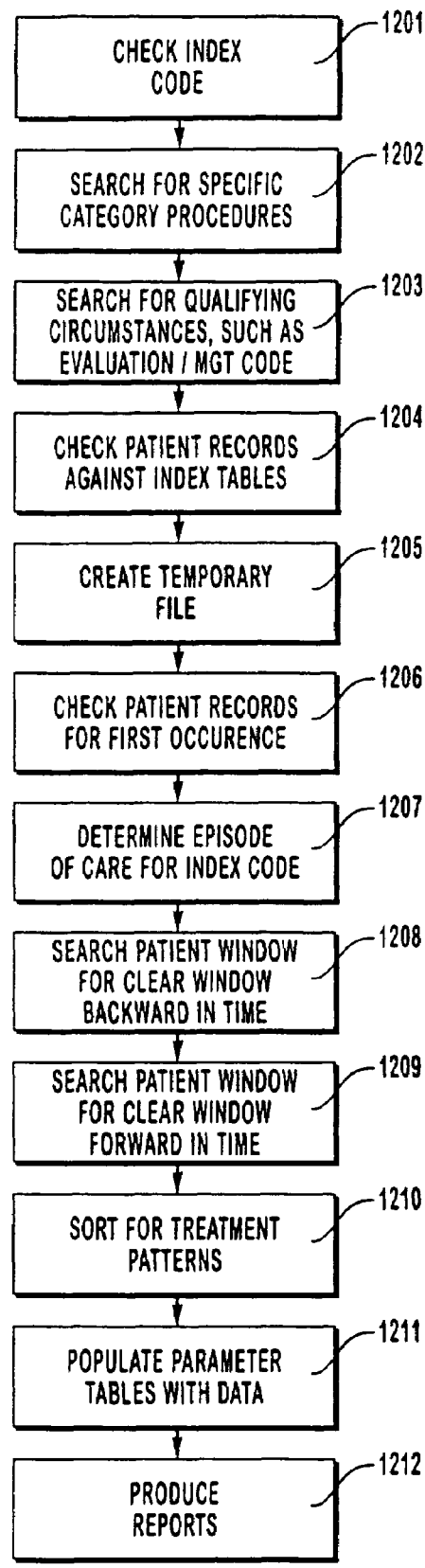
FIG. 12 depicts the process of the preferred embodiment of the Episode of Care element of the invention.

The steps used in the preferred embodiment to determine an episode of care are shown in FIG. 12 and as follows.

a.) Data Sort by Index Code

First, 1201, the raw data set which has undergone RAM processing is sorted by index code (i.e. general diagnosis) to find all patient records with occurrence of a particular index code on at least two different dates of service. Second, 1202, qualifying ICD codes (specific diagnosis) associated with the index code in question are found by searching patient history for at least one occurrence of the specific category or index code, to be considered in the criteria of an episode of care. Third, 1203, during this step patient history records are searched for qualifying circumstances such as procedures relating to specific medical conditions which may have been indicated as usually requiring an Evaluation and Management (E/M) service during the course of treatment. For example, an occurrence of a qualifying circumstance such as an E/M service during the patient history is considered in the criteria of an episode of care. Fourth, 1204, once the data history has been searched for qualifying circumstances, the valid components of these patient records are then checked against the three inter-relational Index Tables to identify qualifying ICD codes associated with the chosen index code. In addition, the patient records are searched for any comorbidity ICD codes that would disqualify the patient record for inclusion in the EOC (such as diabetes with renal failure). Records then are given a staging indicator (i.e. chronic, acute, life-threatening, etc.) associated with the index code to continue in the EOC process in the determination of windows.

Fifth, 1205, a temporary file is created based on combining the authorized and/or disallowed ICD codes that are associated with a given index code in the Index Global Table (listing preventative and aftercare codes) and the Index Detail tables. The temporary file is created using the Index Table Pointers, which determine whether or not the Index Detail Table only should be accessed or whether the Index Global Table is also necessary for drafting the temporary file. Sixth, 1206, for each unique patient record that has been identified as containing the assigned Index code with its associated staging, the entire data set is searched to find the first occurrence of its index code and the date of that record.

b.) Determination of Clear Windows

Clear window processing defines the onset and resolution points of a diagnosis to establish an episode of care. The actual parameters used in clear window processing may vary in various implementations of the invention. Based on the staging indicator, a pre-episode window time period and a post-episode window time period are selected from the table, 1207. Then, 1208, beginning with the first occurrence of an index code in the patient record, a search backward in time is made until no services relating to the diagnosis are found. Then a further search backward in time is made to determine a pre-episode clear window. If any of the ICD codes, V-codes or complications codes found during the data sort by index code processing are found during this search backward in time that fall outside of the pre-episode window time period, there is no clear window and that patient record is rejected and not used. Processing begins again with the sort by index code for a new patient record. If a clear pre-episode window has been found, the patient record continues through post-episode window determination.

Once a clear pre-episode window has been found, a search is made for a clear post-episode window, 1209. This comprises two searches forward in time. The first search is to establish the date of the procedure code in question. Then a further search forward in time is made for the clear post-episode window. If the second search to determine the clear post-episode window reveals any of the ICD codes, V-codes or complications codes found during the data sort by index code processing are found outside of the post-episode window time period (as specified by the staging indicator), there is no clear window and that patient record is rejected and not used. Processing would begin again with the sort by index code for a new patient record. If a clear window has been found the patient record can be analyzed for a valid episode of care.

c.) Valid Episode of Care

The patient record is then checked to determine if the index code in question appears on at least two dates of service. If the index code appears on only one date, the record is rejected. The qualifying tables are then checked to determine if the record meets the minimum criteria for procedure codes (such as surgical services) that are expected to be found within an episode of care for a given index code. If the minimum criteria are not found in an episode of care, the patient record will be rejected and it will not be considered in the profile summary. Processing would then resume with a new patient record and data sort by index code. Once an EOC has been determined for a set of claims history meeting the criteria for an Index code, the information can be sorted by different combinations of treatment patterns that are likely to arise for a given medical condition, 1210. There are eight basic profile classes which outline the common combinations of treatment patterns to statistically analyze and store. These Profile Classes are:

0. Common Profile (diagnostic and E/M services common to all of the above).
1. Surgery/Medicine/Radiation Profile
2. Medicine/Radiation Profile
3. Surgery/Radiation Profile
4. Surgery/Medicine Profile
5. Radiation Profile
6. Medicine Profile
7. Surgery Profile
8. Summary Profile (summary of 0-7 above)

If the patient record contains the minimum criteria for an EOC then processing continues with population of the procedure and category tables.

d.) Populating the Procedure and Category Parameter Tables

Patient records that have not been rejected by this point in the process will be added to the procedure and category tables, 1211. Data from all of the episodes of care for each index code are inserted into the parameter tables to create the summary statistical profiles. In the preferred embodiment these tables are accessed by index code and populated with data from all the episodes of care for each index code to create and provide summary statistics. The information generated is driven by the index code and is sorted chronologically and by category of procedures. The procedure description table and category table are also accessed to determine a description of the procedure codes and the service category in which they fall.

The final step of the EOC process is the generation of output reports, 1212. The output report of this step can be either a on-line look-up report or a hard copy report. Reports are further described below.

The reader is directed to the Microfiche Appendix containing the source code for EOC processing and to FIG. 9 for supplementary information.

At this point, parameter tables have been created which may be accessed for various purposes. A description of these was listed above.

B. Use of the Database

1. Look-Up Function

In the preferred embodiment of the invention, a look-up function is provided so that various information available in the database may be accessed. In general, a specific diagnosis may be reviewed in each of the tables of the database based on ICD code. In various embodiments of the invention, other look-up functions may be provided based on nearly any category of information contained in the database. In the preferred embodiment of the invention display of profiles is performed as part of the look-up function. Information in the procedure and category parameter tables are displayed by index code sorted chronologically to show a profile.

Figure 13:
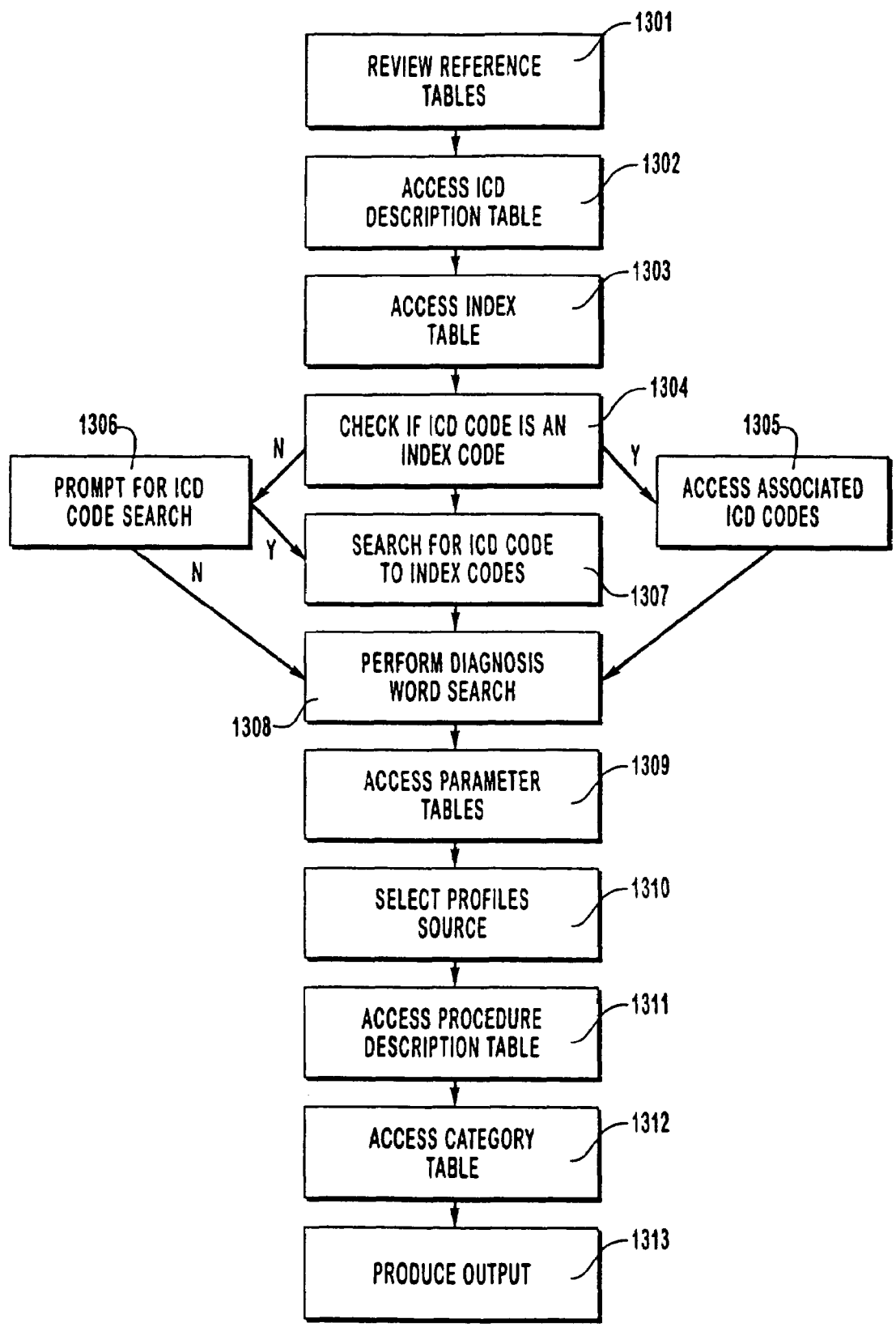
FIG. 13 depicts the process of the preferred embodiment of the Look-up element of the invention.

The specific steps of the preferred embodiment of the Look-Up function of the invention are shown in FIG. 13 and described as follows.

The first step, 1301, is to review the reference tables for a given Index ICD code. Once a specific diagnosis is chosen for review the process moves to step two. In step two, 1302, the ICD description table is accessed to verify that the ICD-9 code is valid, complete and to provide a description of the diagnosis. It will also indicate a risk adjustment factor assigned to the diagnosis.

In step three, the Index tables are accessed, 1303. Next, step four, 1304, is to determine whether or not the chosen ICD code is an Index code. If it is found as an Index code, any additional ICD codes associated which the selected Index code will be accessed, 1305. If a chosen diagnosis is not listed as an index code, a prompt, 1306, will allow a search for the selected ICD code to list which index code(s) it may be associated with and its indicator, 1307. A word search capability, 1308, is included in the look-up function applicable to the Index code display. A word or words of a diagnosis is entered and a search of possible ICD codes choices would be listed.

The next step, 1309, is to access the Parameter Tables to display selected profiles. The information provided is driven by the index code and is sorted chronologically, by profile class and by category of procedures. The user is then given the opportunity to choose whether the profiles to be accessed are from the reference tables, client developed profiles, or both, 1310. Next the Procedure Description Table, 1311, and the Category Table, 1312, are accessed to ascertain description of procedure codes and categories under which they fall.

The last step of the Look-Up function is the output of report product, 1313. This report may either be on-line look-up process or in the hard copy report format.

The preferred embodiment of the invention also performs subset profile look-up. This permits analysis of profiles based on selected subsets of data such as age, gender, region and provider specialty.

Figure 14:
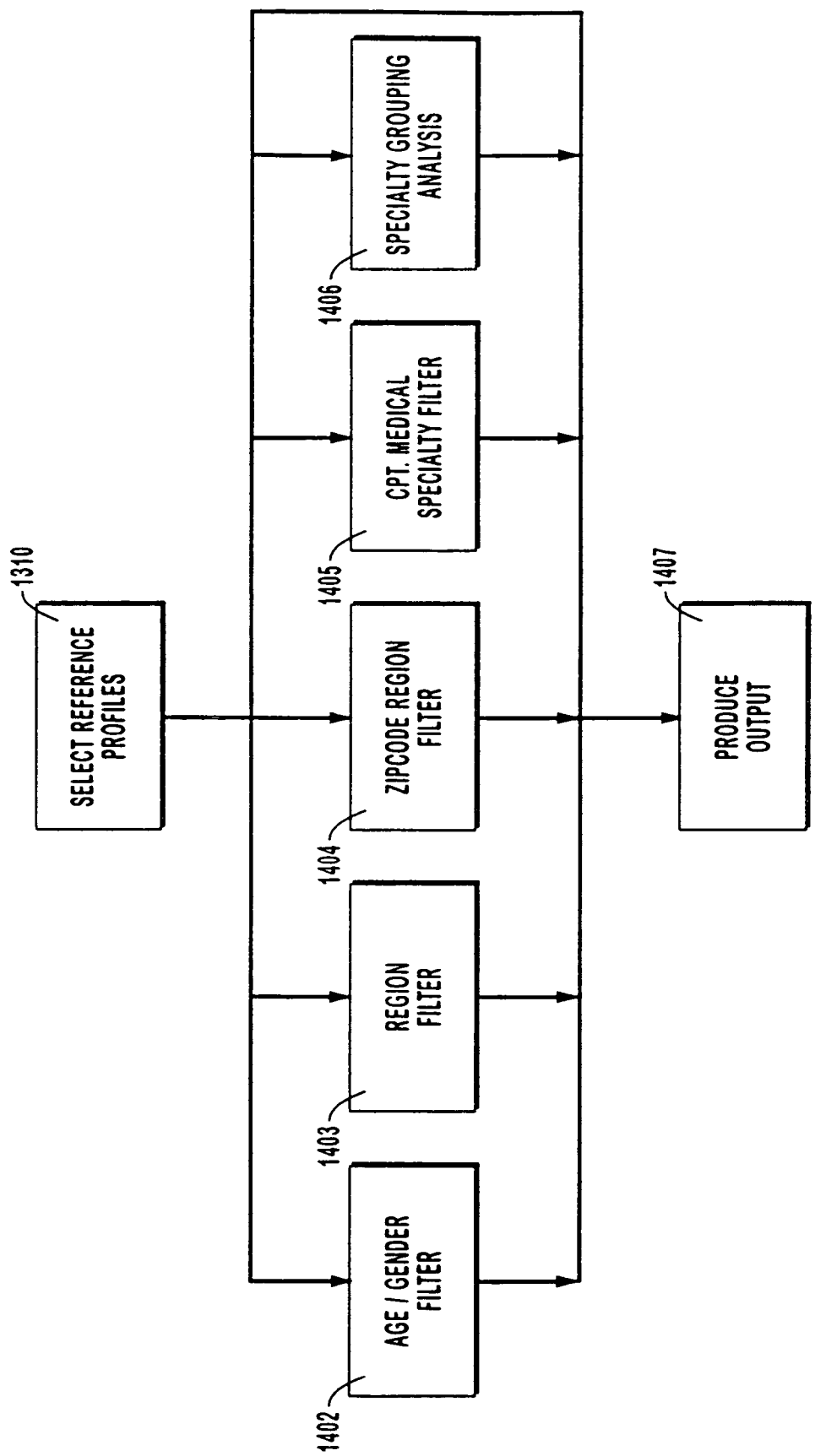
FIG. 14 depicts the process of the preferred embodiment of the Subset Parameter Look-up component of the Look-up element of the invention.

The process for the subset of profiles look-up includes all of the steps necessary for the general profiles look-up and includes the following additional steps shown in FIG. 14 and described below.

The Age/Gender Table is accessed to ascertain the standard age ranges and/or gender selection for a given profile, 1402. This information is stored by index code with an adjustment factor to be multiplied against the occurrence count of each procedure stored in the parameter table. For example, an adjustment factor of 0.6 associated with an age range of 0 to 17 would be calculated against an occurrence count of 10 for CPT code 71021 for Index code 493XX giving an age adjusted occurrence of 6 for that age range.

The Region Statistic Table, 1403, is accessed and used in a similar manner as the Age/Gender Table. This table has adjustment factors based on ten regions throughout the United States.

The Zip/Region Table, 1404, is accessed to identify what region a particular geographic zip code falls within.

The CPT Statistic Table, 1405, is accessed and used in a similar manner as the Age/Gender table. This table has adjustment factors based on different medical specialty groupings.

The Specialty table, 1406, is accessed to ascertain what particular specialty groupings are suggested.

The subset parameter Look-Up function also includes the capability of producing output reports, 1407. These reports can be on-line look-up process reports or hard-copy report format reports.

2. Comparison Processing

In the preferred embodiment of the invention, it is possible to compare profiles developed from a data set against profiles developed from a reference data set. Subsets of profiles may be compared as well. Profiles may be compared for any index code and profile reports may be output. It is also possible to identify those medical providers (whether individuals or institutions) who provide treatment that does not fall within the statistically established treatment patterns or profiles. Further, various treatment patterns for a particular diagnosis can be compared by treatment cost and patient outcome to determine the most effective treatment approach. Based on historical treatment patterns and a fee schedule, an accurate model of the cost of a specific medical episode can be created.

Figure 15:
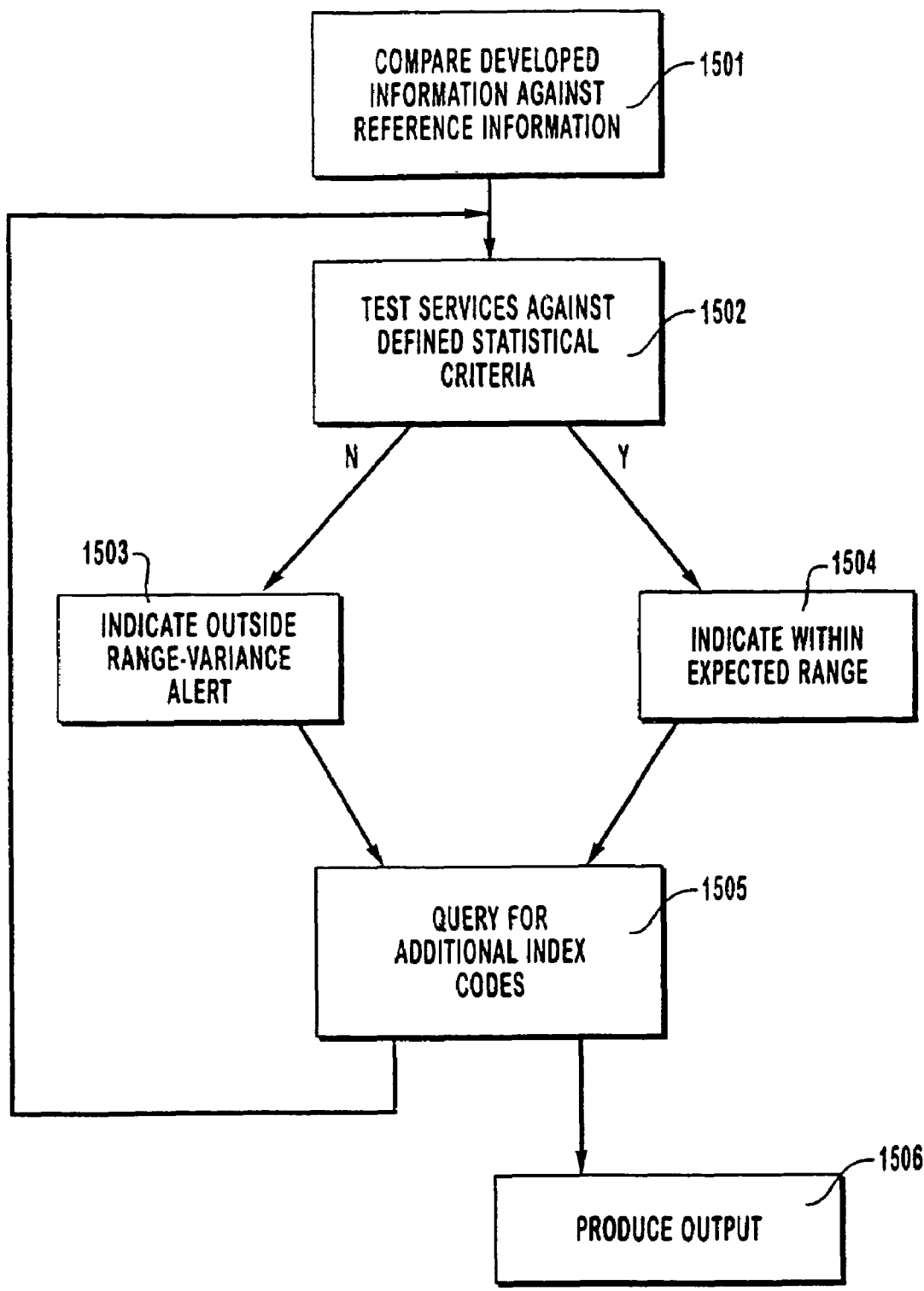
FIG. 15 depicts the process of the preferred embodiment of the Profile Comparison element of the invention.

The specific process of Comparison Processing is shown in FIG. 15 and described as follows. The first step, 1501, is the comparison of information developed from the data history search process with reference information stored in the Parameter Tables. The next step, 1502, is to test the services from the history processing to see if it falls within the defined statistical criteria in the Parameter Tables. If it does an indicator is given to this effect, 1504. If the services fall outside the statistical criteria of the reference Parameters Table, a variance alert describing the difference will be given, 1503. The process may be repeated for each index code and its profile developed in the history process, 1505. The final step is to produce output reports, 1506. These reports are either on-line look-up process reports or hard-copy report format reports.

3. Reporting

Reporting of various information contained in the database is provided in the preferred embodiment. Six different types of reports or displays are provided in the preferred embodiment, these are: Provider Practice Profile Report, Profile Comparison Reports, Resident Parameters Display, Local Parameters Display, Parameter Comparison Report and Chronological Forecast. Each of these reports or displays is described as follows.

The Provider Practice Profile Report is a set of reports which provide a tally or summary of total CPT and/or ICD code utilization by a provider or group of providers during a specified time interval and allows comparison against provided reference data or client generated reference data.

The select criteria for running the tally can be any one of the following:
single physician, department, specialty or clinic by CPT and/or ICD
multiple physicians, departments, specialties, or clinics by specialty, region, CPT and/or ICD
period of time being analyzed Included in the report is the following:
criteria for select
claims analyzed
average lines per bill
invalid CPTs and percent of total for study
invalid ICDs and percent of total for study
incomplete ICDs and percent of total for study
patients in age categories
patients by gender
missing ICDs and percent of total for study The report includes numerous (up to about 22 in the preferred embodiment) separate procedure (such as CPT) categories which are headers for each page. Each CPT utilized within that category will be reported by:
frequency and percent of total
dollar impact and percent of total for single or multiple fee schedules and/or allowable reimbursement schedules
grand total if more than a single physician report The report includes a tally by ICD. Each ICD utilized is reported on by:
frequency and percent of total
dollar impact and percent of total for single or multiple fee schedule and/or allowable reimbursement schedules (dollar impact based on each line item CPT correlated to the ICD)

If a report includes region and/or specialty, there are numerous tallies for procedure categories and/or ICD.

The Profile Comparison Reports give the client a comparison of a health care provider's (or group of providers') utilization of CPT and/or ICD-9 codes in a specific episode of care against a reference set of utilization profiles. This includes number, frequency and chronological order of services along with other statistical information (eg, range, mode, confidence interval, etc . . . ).

The comparison can be against one of the following:
national norms resident in the tables
regional norms resident in the tables
client established norms developed by use of the tally report, outlined above
other Selection criteria include the following:
single physician, department, clinic or specialty by CPT and/or ICD to be compared against national, regional, specialty, and/or client established norms
multiple physicians, departments, clinics, or specialties by CPT and/or ICD by specialty and/or region, to be compared against national, region, specialty, and/or client established norms
set period of time being analyzed General information included in the report includes:
criteria for select (ie, national, regional, specialty, and/or client established)
claims analyzed
average lines per bill
invalid CPTs and percent of total for study and comparison
invalid ICDs and percent of total for study and comparison
incomplete ICDs and percent of total for study and comparison
patients in age categories and comparison
patients by gender and comparison
missing ICDs and percent of total for study and comparison The report includes numerous separate CPT categories which are headers for each page. Each CPT utilized within that category will be reported by:
frequency and percent of total
dollar impact and percent of total for single or multiple fee schedules and/or allowable reimbursement schedules
grand total if more than a single physician report The report includes a tally by ICD. Each ICD utilized is reported on by:
frequency and percent of total
dollar impact and percent of total for single or multiple fee schedule and/or allowable reimbursement schedules (dollar impact based on each line item CPT correlated to the ICD)

If a report includes region and/or specialty, there are numerous tallies for CPT categories and/or ICD.

The Resident Parameters Display provides the client a look-up mode for information stored in the Practice Parameter Tables or client generated parameter tables. This look-up should be on the computer screen or as a print out.

The selection criteria is based on the key elements of the Practice Parameter tables. For Example:
Index code for associated CPT codes and/or any other the following:
index code only
index code and indicators (ie, related, complicating, rule/outs, symptoms, etc)
specialty
region
age
gender
standard length of Episode of Care
based on profile (tally)
based on parameter (timeline)
regional variables
other misc. look-ups
geozips incorporated in a region
CPT for follow up days and/or lifetime occurrence
specialty and associated CPT codes
ICD and Risk Factor The Local Parameters Display provides the same information as described in the Display of Resident Parameters listed above.

The Parameter Comparison Reports are a set of reports which give the client a comparison of a physician (or group of physicians) utilization of CPT and/or ICD against an existing set of utilization norms over a timeline and in chronological order.

The comparison can be against one of the following:
national norms resident in the tables
regional norms resident in the tables
client established norms developed by use of the tally report, outlined above
other
  Selection criteria include the following:
single physician, department, clinic or specialty by CPT and/or ICD to be compared against national, regional, specialty, and/or client established norms
multiple physicians, departments, clinics, or specialties by CPT and/or ICD by specialty and/or region, to be compared against national, region, specialty, and/or client established norms
set period of time being analyzed
  General information included in the report includes:
criteria for select (ie, national, regional, specialty, and/or client established)
claims analyzed
average lines per bill
invalid claims due to incomplete Episode of Care
invalid CPTs and percent of total for study and comparison
invalid ICDs and percent of total for study and comparison
incomplete ICDs and percent of total for study and comparison
patients in age categories and comparison
patients by gender and comparison
missing ICDs and percent of total for study and comparison The report includes numerous separate procedure categories which are headers for each page. Each procedure category utilized within that category will be reported by:
frequency and percent of total
dollar impact and percent of total for single or multiple fee schedules and/or allowable reimbursement schedules
grand total if more than a single physician report The Chronological Forecast provides statistical trend analysis and tracking of the utilization of billing codes representative of services performed by a physician for a given diagnosis over a set period of time and stored in chronological order. It will provide a summation of billed codes representative of services and diagnoses utilized by an entity over a period of time.

C. System Requirements

The method and system of this invention may be implemented in conjunction with a general purpose or a special purpose computer system. The computer system used will typically have a central processing unit, dynamic memory, static memory, mass storage, a command input mechanism (such as a keyboard), a display mechanism (such as a monitor), and an output device (such as a printer). Variations of such a computer system could be used as well. The computer system could be a personal computer, a minicomputer, a mainframe or otherwise. The computer system will typically run an operating system and a program capable of performing the method of the invention. The database will typically be stored on mass storage (such as a hard disk, CD-ROM, worm drive or otherwise). The method of the invention may be implemented in a variety of programming languages such as COBOL, RPG, C, FORTRAN, PASCAL or any other suitable programming language. The computer system may be part of a local area network and/or part of a wide area network.

It is to be understood that the above-described embodiments are merely illustrative of numerous and varied other embodiments which may constitute applications of the principles of the invention. Such other embodiments may be readily devised by those skilled in the art without departing from the spirit or scope of this invention and it is our intent that they be deemed within the scope of our invention.

We claim:

1. A computer-implemented process for processing medical claims comprising a computer performing the following:
   (a) reading medical claim data, input as at least one of a plurality of data records, into a computer memory;
   (b) validating each of the at least one of a plurality of data records for at least one of a diagnosis code and a treatment code;
   (c) reading at least one pre-defined relationship between the at least one of a diagnosis code and a treatment code in the validated at least one of a plurality of data records and pre-defined episode treatment categories;
   (d) grouping the validated at least one of a plurality of data records to an episode treatment category based upon the pre-defined relationship, each episode treatment category having a dynamic time window defining a time period during which validated at least one of plurality of data records may be grouped to an episode treatment category; and
   (e) classifying the patient data records into at least one of a plurality of episode treatment groups, each of the plurality of episode treatment groups being defined by an episode treatment category.

2. The process as claimed in claim 1 wherein an active and open episode treatment group comprises an episode treatment group number, sequential episode number, and most recent anchor date of treatment.

3. The process as claimed in claim 1 wherein step (d) further comprises the step of identifying claim records as one of management, surgery, facility, ancillary, and prescription drug records.

4. A computer-implemented process for processing medical claims comprising a computer performing the following:

(a) reading a first patient's medical claim data, input as at least one of a plurality of data records, into a computer memory;

(b) validating each of the at least one of a plurality of data records for at least one of a diagnosis code and a treatment code;

(c) reading at least one pre-defined relation between the at least one of a diagnosis code and a treatment code in the validated at least one of a plurality of data records and pre-defined medical episodes; and (d) grouping the validated at least one of a plurality of data records to at least one of a plurality of episode treatment groups, each of the at least one of a plurality of episode treatment groups further comprising an episode treatment group identifier, a most recent anchor from date of treatment and a most recent sequential anchor record count.

* * * * *

UNITED STATES PATENT AND TRADEMARK OFFICE
CERTIFICATE OF CORRECTION

PATENT NO. : 7,774,252 B2
APPLICATION NO. : 11/512003
DATED : August 10, 2010
INVENTOR(S) : Jerry G. Seare et al.

It is certified that error appears in the above-identified patent and that said Letters Patent is hereby corrected as shown below:

SPECIFICATION

| Column | Line | PTO | Should Read |
| --- | --- | --- | --- |
| 3 | 11 | Chinsky, "patterns of Treatment | Chinsky, "Patterns of Treatment |
| 3 | 28 | Reguestors | Requestors |
| 19-20 | 4 [# in chart] | May be an encrypted of | May be an encrypted or |
| 19-20 | 16 [# in chart] | 18. Modifier | 16. Modifier |
| 19-20 | 18 [# in chart] | Medicald etc. | Medicaid etc. |
| 22 | 60 | step in transporting raw data | step in transforming raw data |

Signed and Sealed this

Twenty-first Day of December, 2010

David J. Kappos
*Director of the United States Patent and Trademark Office*